US006322780B1

(12) United States Patent
Lee et al.

(10) Patent No.: US 6,322,780 B1
(45) Date of Patent: Nov. 27, 2001

(54) MAREK'S DISEASE VIRUS VACCINES FOR PROTECTION AGAINST MAREK'S DISEASE

(75) Inventors: Lucy F. Lee, East Lansing, MI (US); Keyvan Nazerian, Skokie, IL (US); Richard L. Witter, Okemos; Ping Wu, East Lansing, both of MI (US); Noboru Yanagida, Nakahara-ku; Shigeto Yoshida, Kamakura, both of (JP)

(73) Assignees: The United States of America as represented by the Secretary of Agriculture, Washington, DC (US); Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 08/709,731

(22) Filed: Sep. 9, 1996

Related U.S. Application Data

(63) Continuation of application No. PCT/US96/11360, filed on Jul. 5, 1996, and a continuation-in-part of application No. 08/499,474, filed on Jul. 7, 1995, now abandoned.

(51) Int. Cl.[7] .......................... A61K 48/00; A01N 63/00; C12N 7/01

(52) U.S. Cl. .................. 424/93.2; 424/93.21; 435/235.1; 435/320.1; 536/23.72

(58) Field of Search ............................ 424/139.1, 159.1, 424/147.1, 184.1, 186.1, 199.1, 204.1, 229.1, 231.1, 230.1, 93.2, 93.21; 435/71.1, 69.1, 69.3, 89, 172.3, 239, 235.1, 320.1; 536/23.72

(56) References Cited

U.S. PATENT DOCUMENTS 5,369,025 11/1994 Nazerian et al. .
5,403,582 4/1995 Nazerian et al. .

FOREIGN PATENT DOCUMENTS 90-02803 * 3/1990 (WO) ............................ C12N/15/38

OTHER PUBLICATIONS

Ross et al. (1991), Journal of General Virology, 72:939–947.

Ross et al. (1989), Journal of Gen. Virology, 70:1789–1804.

Boyle et al. (1988), Virus Research, 10:343–356.

Okazaki et al. (1970), Avian Dis. 14:413–429.

Churchill et al. (1969), Nature, vol. 221: 744–747.

Schat et al. (1978), J. Nat. Cancer Inst., vol. 60, No. 5, pp. 1075–1081.

Rispens et al., (1972), Avian Disease, 16:108–125.

Blacklaws et al. (1990), Virology, 177:727–736.

Witter et al. (1979), Avian Pathology, 8:145–156.

Coussens et al., J. of Virology, vol. 62, No. 7, pp 2373–2379, Jul. 1988.*

Cui et al., J. of Virology, vol. 65, No. 12 pp 6509–6515 Dec. 1991.*

Ogawa et al. Recombinant fowlpox viruses inducing protective immunity against Newcastle disease and fowlpox viruses. Vaccine. vol. 8, pp 486–490, Oct. 1990.*

Igarashi et al. Restriction Enzyme Map of Herpesvirus of Turkey DNA and its Collinear relationship with Marek's Disease Virus DNA. Virology. vol. 157, pp 351–358, 1987.*

Chang et al. Properties of the Protein Encoded by the UL32 Open Reading Frame of Herpes Simplex Virus I. Journal of Virology. vol. 70, No. 6, pp 3938–3946, Jun. 1996.*

Chang et al. The Product of the UL31 Gene of Herpes Simplex Virus 1 Is a Nuclear Phosphoprotein Which Partitions with the Nuclear matrix. Journal of Virology. vol. 67, No. 11, pp 6348–6356, Nov. 1993.*

Whittaker et al. Glycoprotein 300 in encoded by gene 28 of equine herpesvirus type 1: a new family of herpesvirus membrane proteins? Journal of General Virology. vol. 73, pp 2933–2940, 1992.*

Witter. Influence of serotype and virus strain on synergism between Marek's disease vaccine viruses. Avian Pathology. vol. 21, pp 601–614, 1992.*

Zelnick. Marek's Disease and New Approaches to its Control. Acta virologica. vol. 39, pp 53–63, 1995.*

Boyle et al. Recombinant fowlpox virus vaccines for poultry. Immunology and Cell Biology. vol. 71, pp 391–397, 1993.*

Nazerian et al. Protection against marek's Disease by a Folwpox Virus Recombinant Expressing the Glycoprotein B of Marek's Disease Virus. Journal of Virology. vol. 66, No. 3, pp 1409–1413, Mar. 1992.*

Reddy et al. Protective efficacy of a recombinant herpesvirus of turkeys as an in ovo vaccine against Newcastle and Marek's disease in specific pathogen free chickens. Vaccine. vol. 16, No. 6, pp 469–477, 1996.*

Yanagida et al. Recombinant Fowlpox Viruses Expressing the Glycoprotein B Homolog and the pp38 Gene of Marek's Disease Virus. Journal of Virology. vol. 66, No. 3, pp 1402–1408, Mar. 1992.*

* cited by examiner

*Primary Examiner*—James O. Wilson
(74) *Attorney, Agent, or Firm*—Birch, Stewart, Kolasch & Birch, LLP

(57) ABSTRACT

A nucleotide sequence encoding the gp82 polypeptide of Marek's disease virus is disclosed. Also disclosed are recombinant viruses which are useful as vaccines for protecting against Marek's Disease, preferably containing two or more genes encoding Marek's Disease Virus antigens such as glycoprotein B and glycoprotein gp82, under the control of a poxvirus promoter within a region of the DNA of fowlpox virus which is not essential for virus growth. Also provided is a vaccine exhibiting a synergistic immunoprotective effect, comprising a recombinant fowlpox virus expressing Marek's Disease Virus gB protein in combination with turkey herpesvirus. A method of immunizing poultry, comprising administering any of the disclosed vaccines, is also provided.

15 Claims, 17 Drawing Sheets

MDV genome
BamHI Map
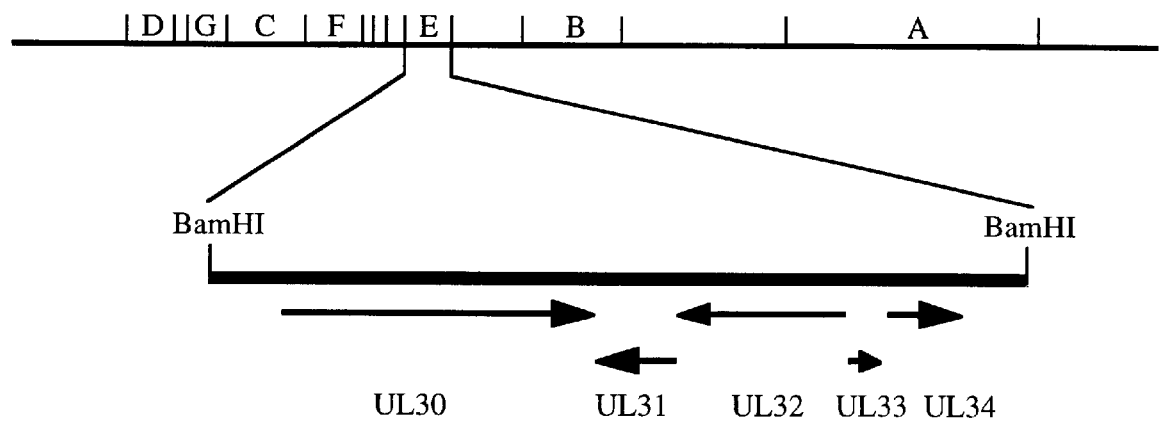
Figure 1

```
ATGGCCAACCGCCCTACAGAGTTGGCAGCTTTTATCCGATCTTCTGGAGAAGCA
GATGGATGGATAGAGGAGTCCTTCAAAGAACCCTATGTGGCATTTAATCCGGAC
GTCTTGATGTATAATGACACGCTTTTTAACGAGTTATTACTCTCCGCCCACGCG
CTCAAGATCAACAGTATACAGGATGTTCAGAGTGATGATACCGTGGAGGATGCG
GGAGATATTGGGAATGAAGTTATACATTCGGAATTAGTAACTTTTATAGAGACT
GCTGCAGATGTTTATGCCTTAGATCGTCAATGCCTTGTTTGTCGTGTGCTAGAT
ATGTACAGGCGCAATTTCGGTTTATCAGCTCTATGGATGGCAGATTATGCTTTT
TTATGTTCCAAATGTCTTGGTTCTCCACCATGTGCAACTGCAACCTTTATAGCC
GCGTTTGAATTCGTATATATAATGGATAAACACTTTCTATCCGATCATGGTTGT
ACACTCGTACGCTCCTTTGGAAAAAAACTTTTAACTCTCGAAGATATTCAGAGA
CATTTTTTTCTGCATGGCTGTTTTCGAACGGACGGGGCGTTCCTGGACGACGC
CATGATGAAGTTATTACGTCTCGTTCTAAGCAAGGACGATTAGTAGGGCGACGT
GGGAAATTTTCTACTGCGGGTGATGCCAAAGTCTTGTACAGTAATTACTCATAT
TTAGCTCAGAGTGCTACACGAGCCCTGTTAATGACCTTATCTGATTTAGGTTCT
GCACCGCTAGAAGTTATCGAAGGGCGACAAAAGTCTATTTCGGGGGATGTTCGA
AATGAGTTGAGGGATGGCATAGAGAGTAGGAAAAGGGTCGCGCATGTCATTCAT
TCCGTTGGACCAGTCCACTCATGCCCAACTACTCTTTCCGTTGCTTTGGCGGGC
TGGAAAGATTGTGCTAAAAACGTAGAATGTAACTTTTTTCAACTGGAAAGTTGT
ACTTTGCGCGCATCGTCCGAGGATAATGATTATGAACACGAGTGGGAACTCCGA
GCAAGTGAAGAAAGTTAAATGTGGTGGAAAATGTTCAGGACATGCAACAGATA
GATGCGTCTCAATGCGAACATCATGAACATGCAAGAAATGAGGATTGTACAATG
GGTTATGGCAACCTCGTTTTATTGTTATTAGCGGGAACGGGGTCTGCACCTGAG
GCAGCGAGCGAACTCGCATTCATGGCCGCAAAAGTTAGAAGGGAAACGGTGGAT
ATATTTTGGAAAAATCATAGAAGGGAATTTGCTAATGACGTTACTGCAGCATAC
AGTGCATGTTACGGTGAGGATTCGGAACCCGATTTAGAGTTAGGCCCATTGATG
ATAACACAGTTAAAGCACGCGATAACAAAAGGAGGAACATCTGCGGAGTGTTTA
TTATGTAACCTGCTGCTGATACGTACATATTGGCTGGCAATGCGTAAATTTAAA
CGCGATATCATCACATATTCCGCCAACAATATAGGTTTATTTCATAGCATAGAA
CCTGTTCTAGATGCTTGGCGATCACAGGGACATCGTACAGATTTGGGGGACGAA
GGATGTTTTGTAACATTAATGAAAAGCGCGGGAACGGAGGCCATTTATAAACAC
CTATTCTGCGATCCAATGTGTGCGGCACGAATAGCCCAGACCAATCCACGATCG
TTATTTGATCACCCAGATGCCACCAATCATGACGAACTAGCATTATATAAAGCC
CGTCTCGCCAGTCAGAACCATTTTGAAGGTCGCGTATGTGCTGGACTTTGGGCT
TTGGCGTATACGTTTAAAACTTATCAGGTCTTTCCTCCCCGTCSAACCGCACTG
TCTGCTTTCGTTAAAGACGCTGGGGCATTGTTGCAAAGACATTCCATCTCCTTG
ATATCTCTCGAGCATACATTAGGAGTCTACGTGTAA
```

Figure 2

```
MANRPTELAAFIRSSGEADGWIEESFKEPYVAFNPDVLMYNDTLFNELLLSAHA
LKINSIQDVQSDDTVEDAGDIGNEVIHSELVTFIETAADVYALDRQCLVCRVLD
MYRRNFGLSALWMADYAFLCSKCLGSPPCATATFIAAFEFVYIMDKHFLSDHGC
TLVRSFGKKLLTLEDIQRHFFLHGCFRTDGGVPGRRHDEVITSRSKQGRLVGRR
GKFSTAGDAKVLYSNYSYLAQSATRALLMTLSDLGSAPLEVIEGRQKSISGDVR
NELRDGIESRKRVAHVIHSVGPVHSCPTTLSVALAGWKDCAKNVECNFFQLESC
TLRASSEDNDYEHEWELRASEEKLNVVENVQDMQQIDASQCEHHEHARNEDCTM
GYGNLVLLLAGTGSAPEAASELAFMAAKVRRETVDIFWKNHRREFANDVTAAY
SACYGEDSEPDLELGPLMITQLKHAITKGGTSAECLLCNLLLIRTYWLAMRKFK
RDIITYSANNIGLFHSIEPVLDAWRSQGHRTDLGDEGCFVTLMKSAGTEAIYKH
LFCDPMCAARIAQTNPRSLFDHPDATNHDELALYKARLASQNHFEGRVCAGLWA
LAYTFKTYQVFPPRXTALSAFVKDAGALLQRHSISLISLEHTLGVYV
```

Figure 3

MAREK'S DISEASE VIRUS VACCINES FOR PROTECTION AGAINST MAREK'S DISEASE

CROSS-REFERENCE TO RELATED APPLICATIONS

This application is a continuation of PCT Application No. PCT/US96/11360 filed on Jul. 5, 1996 which designated the United States, and a continuation-in-part of U.S. Ser. No. 08/499,474 filed on Jul. 7, 1995, now abandoned priority of which applications is claimed under 35 U.S.C. §120. The entire contents of both of these applications are incorporated by reference.

BACKGROUND OF THE INVENTION

1. Field of the Invention

The present invention relates to a gene derived from Marek's disease virus having a unique nucleotide sequence, recombinant viruses containing this gene, poultry vaccines utilizing this gene, and recombinant fowlpox vaccines that exhibit a syngeristic effect in protecting against Marek's disease.

2. Description of Related Art

Marek's disease (MD) is a highly contagious neoplastic disease of domestic chickens that affects chickens worldwide and causes high mortality and condemnation if chickens are not vaccinated at one day of age. MD is caused by a highly cell-associated oncogenic herpesvirus known as Marek's disease virus (MDV).

A number of live virus cell-associated vaccines are available that protect chickens against MD. These vaccines are maintained and administered in delicate, cell-associated form. The vaccines need special handling, and must be stored and transported in a frozen state in liquid nitrogen in order to maintain their viability and efficacy. These existing vaccines must be maintained and administered in cell-associated form, a condition that is costly and cumbersome.

The known vaccines contain the entire MDV genome, including sequences related to induction of patho-genesis. Although the existing vaccines against MD are either attenuated or are naturally apathogenic, viral mutation is known to occur in herpesviruses, and there is a possibility that virulent pathogenic mutants may emerge in such vaccines. Such mutants could be less effective and even harmful.

Churchill et al. (*Nature* 221:744–747 (1969)) and Okazaki et al. (*Avian Dis.* 14:413–429 (1970)) developed the first effective and safe vaccines against MD. These vaccines have been in use for the last 20 years, and have reduced losses to the poultry industry worldwide. Other candidate vaccines based on serotype 2 naturally apathogenic MDV (Schat et al. *J. Natl. Cancer Inst.* 60: 1075–1082 (1978)), or newly attenuated serotype 1 MDV (Rispens et al. *Avian Dis.* 16:108–125 (1972)), and combinations of these viruses as bivalent vaccines (Witter *Avian Dis.* 31:252–257 (1987)), have helped provide better protection against MD. All these vaccines, except the herpesvirus of turkeys (HVT) vaccine, require storage and transportation in a frozen state in liquid nitrogen,and have to be administered as infected cells, which calls for careful procedures to prevent inactivation of the vaccine. Even in the case of HVT vaccine, cell-associated viruses have been most widely used because they are more effective than cell-free virus in the presence of maternal antibodies (Witter et al. *Avian Pathol.* 8:145–156 (1978)).

Recombinant DNA technology has facilitated the construction of recombinant vaccines that contain only those desired viral genes or gene products that induce immunity without exposing the animal to genes that may induce pathological disorders. Pox viruses, including avipox virus, especially fowlpox virus (FPV), provide excellent models for such vaccines. These viruses have a large DNA molecule with numerous non-essential regions that permit the insertion of several immunogenic genes into the same virus for the purpose of creating multivalent vaccines. These multivalent vaccines may induce cell-mediated as well as antibody-mediated immune response in a vaccinated host. Vaccinia virus (W) has been used extensively for this purpose, and a number of VV recombinants have been constructed that express a variety of foreign genes, including those that elicit neutralizing antibodies against glycoproteins of herpes simplex virus (HSV) type 1 (Blacklaws et al. *Virology* 177:727–736 (1990)). Similarly, there are a number of reports describing the expression of foreign genes by recombinant FPV (Boyle et al. *Virus Res.* 10:343–356 (1988) and Ogawa et al. *Vaccine* 8:486–490 (1990)). Recently, we demonstrated that the recFPVgB protected chickens against MDV challenge (Nazerian et al. *J. Virol.* 66:1409–1413 (1992)).

MDV homologues of the HSV genes coding for glycoproteins B, C, D, H, and I, E, L (gB, gC, gD, gH and gI, gE, gL) have recently been cloned and sequenced (Coussens et al. *J. Virol.* 62:2373–2379 (1988); Ross et al. *J. Gen. Virol.* 70:1789–1804 (1989); Ross et al. *J. Gen. Virol.* 72:939–947 (1991); Ross et al., International Publication No. WO 90/02803 (1990); Brunovskis and Velicer, *Virology* 206:324–338 (1995); and Yoshida et al. *Virology* 204:414–419 (1994)).

SUMMARY OF THE INVENTION

The present inventors have shown that gB is an important gene for protective immunity against MD (Nazerian et al. *J. Virol.* 66:1409–1413 (1992)). Whittaker et al. (1992) reported that Equine herpesvirus type 1 (EHV-1) gene 28 encodes a glycoprotein, gp300, that is homologous to the HSV-1 UL32, and functions in EHV-1 in cell-to-cell fusion processes. We postulated that if such a homologous gene existed in MDV, it may function in cell to cell fusion since MDV is a cell-associated virus. Recently, we identified and sequenced an MDV gene homologous to HSV-1 UL32, and identified an O-linked glycoprotein, gp82, in MDV-infected cells belonging to a class of membrane proteins (Lee, unpublished data).

The present invention relates to the MDV UL32 gene encoding a membrane glycoprotein. The DNA sequence of the UL32 gene is shown in SEQ ID NO:1 in the attached Sequence Listing. The present invention therefore relates to this sequence, which encodes a protein in accordance with the degeneracy of the genetic code, preferably in a cloned, isolated, or purified form, and biologically functional variants thereof. The present invention also relates to recombinant DNA molecules comprising the UL32 sequence.

The present invention also relates to novel recombinant viral vaccines, such as recombinant FPV, HVT (herpesvirus of turkeys), MDV, and ILTV (infectious laryngotracheitis virus), that contain the novel UL32 gene encoding membrane glycoprotein gp82 of MDV. Preferably, the vaccine is based on a recombinant FPV containing the UL32 gene of MDV. More preferably, the recombinant FPV contains an additional gene, i.e., the gB gene, encoding gp100, gp60 and gp49, which provides a synergistic effect in protecting against MD in chickens. As shown below, recombinant FPV expressing UL32 is effective against MD. The sequence and the effectiveness of gB as a vaccine has been described in U.S. Pat. No. 5,369,025. The expression of these two genes in cells results in an unexpectedly strong synergistic protective effect against MD in the natural host (chickens). In addition, the vaccine also protects against fowlpox.

The present invention also relates to recombinant FPV vaccines against MD in which the gB gene of MDV or the UL32 gene of MDV or other genes such as those coding for glycoprotein E homologue, glycoprotein I homologue, and other glycoproteins from different serotypes of MDV are inserted into FPV for the purpose of creating a broad-spectrum vaccine effective against several isolates of MDV.

The present invention also relates to a cell-free vaccine against MD containing recombinant (rec) FPV that can be lyophilized, stored, and used under normal conditions, thereby obviating costly and laborious procedures of storing the vaccine in liquid nitrogen, delicate handling, and administering which are necessary with existing cell-associated MD vaccines. For example, after lyophilization, the vaccine of the present invention can be stored, handled, and transported at ambient temperature (20–22° C.), and stored at 4° C. for prolonged periods of time. The vaccine can also be stored in a frozen state wherein the cell-free recombinant virus is present in an aqueous solution which is frozen and stored at, for example, −20° C. or −70° C.

Accordingly, it is an object of the present invention to provide an isolated, purified DNA molecule comprising the nucleotide sequence shown in SEQ ID NO:1, or a nucleotide sequence biologically functionally equivalent thereto.

Another object of the present invention is to provide an isolated, purified DNA molecule comprising a nucleotide sequence encoding a polypeptide having the amino acid sequence shown in SEQ ID NO:2, or encoding a polypeptide biologically functionally equivalent thereto.

Another object of the present invention is to provide an isolated, purified polypeptide having the amino acid sequence shown in SEQ ID NO:2, or a polypeptide biologically functionally equivalent thereto.

Another object of the present invention is to provide a recombinant vector comprising the aforementioned DNA molecules.

Another object of the present invention is to provide a recombinant virus that expresses said DNA molecules. The recombinant virus can further express a nucleotide sequence encoding at least one antigen of an avian pathogen, or a nucleotide sequence biologically functionally equivalent thereto.

Another object of the present invention is to provide a recombinant virus that expresses a DNA sequence encoding a membrane glycoprotein of Marek's Disease virus.

Another object of the present invention is to provide a vaccine composition, comprising a member selected from the group consisting of:
  an isolated, purified DNA molecule comprising the nucleotide sequence shown in SEQ ID NO:1, or a nucleotide sequence biologically functionally equivalent thereto;
  an isolated, purified DNA molecule comprising a nucleotide sequence encoding a polypeptide having the amino acid sequence shown in SEQ ID NO:2, or a polypeptide biologically functionally equivalent thereto;
  an isolated, purified polypeptide having the amino acid sequence shown in SEQ ID NO:2, or a polypeptide biologically functionally equivalent thereto;
  a recombinant vector comprising an isolated, purified DNA molecule comprising the nucleotide sequence shown in SEQ ID NO:1, or a nucleotide sequence biologically functionally equivalent thereto;
  a recombinant vector comprising an isolated, purified DNA molecule comprising a nucleotide sequence encoding a polypeptide having the amino acid sequence as shown in SEQ ID NO:2, or a polypeptide biologically functionally equivalent thereto;
  a recombinant virus that expresses an isolated, purified DNA molecule comprising the nucleotide sequence shown in SEQ ID NO:1, or a nucleotide sequence biologically functionally equivalent thereto;
  a recombinant virus that expresses an isolated, purified DNA molecule comprising a nucleotide sequence encoding a polypeptide having the amino acid sequence as shown in SEQ ID NO:2, or a polypeptide biologically functionally equivalent thereto; and
  a recombinant virus that expresses an isolated, purified DNA molecule comprising the nucleotide sequence shown in SEQ ID NO:1, or a nucleotide sequence biologically functionally equivalent thereto, and which further expresses a nucleotide sequence encoding at least one antigen of an avian pathogen, and a pharmaceutically acceptable carrier.

A vaccine composition of the present invention is most preferably effective for immunizing the vaccinated subject even in the presence of transfer antibodies conferred from the mother of the subject.

Yet another object of the present invention is to provide a vaccine composition, comprising a member selected from the group consisting of:
  a recombinant virus that expresses an isolated, purified DNA molecule comprising the nucleotide sequence shown in SEQ ID NO:1, or a nucleotide sequence biologically functionally equivalent thereto, and gB antigen of Marek's disease virus or a polypeptide biologically functionally equivalent thereto, and
  a virus that expresses an isolated, purified DNA molecule comprising a nucleotide sequence encoding a polypeptide having the amino acid sequence as shown in SEQ ID NO:2, or a polypeptide biologically functionally equivalent thereto, and gB antigen of Marek's disease virus or a polypeptide biologically functionally equivalent thereto, and a pharmaceutically acceptable carrier.

Another object of the present invention is to provide a vaccine composition, comprising isolated, purified nucleotide sequences encoding antigens from avian pathogens, wherein said vaccine composition exhibits an immunoprotective effect greater than the sum of the individual immunoprotective effects of vaccine compositions individually comprising each of said isolated, purified nucleotide sequences encoding antigens from avian pathogens, and a pharmaceutically acceptable carrier.

Another object of the present invention is to provide a vaccine composition, comprising a recombinant virus expressing an isolated, purified nucleotide sequence encoding a Marek's disease virus polypeptide or a biologically functionally equivalent polypeptide, in combination with a herpesvirus, wherein said vaccine composition exhibits an immunoprotective effect greater than the sum of the individual immunoprotective effects of vaccine compositions individually comprising each of said viruses, and a pharmaceutically acceptable carrier.

A still further object of the present invention is to provide a vaccine composition, comprising a member selected from the group consisting of:
  a DNA molecule having the sequence shown in SEQ ID NO:1 or a sequence biologically functionally equivalent thereto;

a recombinant vector that contains a DNA molecule having the sequence shown in SEQ ID NO:1 or a sequence biologically functionally equivalent thereto;

a recombinant virus or viruses that contains a DNA molecule having the sequence shown in SEQ ID NO:1 or a sequence biologically functionally equivalent thereto, as well as a DNA sequence encoding at least one antigen of an avian pathogen, or a nucleotide sequence biologically functionally equivalent thereto; and a polypeptide having the amino acid sequence shown in SEQ ID NO:2, or a polypeptide biologically functionally equivalent thereto, and a pharmaceutically acceptable carrier.

Yet another object of the present invention is to provide a method of immunizing poultry, comprising administering to said poultry any of the vaccines of the present invention.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which:

FIG. 1 shows the location of the UL32 gene homologue in the genome of MDV. The upper part of the figure is a schematic representation of the MDV genome. Abbreviations: TRL: terminal repeat adjacent to unique long region; UL: unique long region; IRL: internal repeat adjacent to unique long region; IRS: internal repeat adjacent to unique short region; US: unique short region; TRS: terminal repeat adjacent to unique short region. The middle part of the figure shows the corresponding BamHI map of the MDV genome. The lower part of the figure shows details of the BamHI-E fragment containing the UL30, UL31, UL32, UL33, and UL34 homologues. Arrows indicate the locations of the five genes, and point in their transcriptional directions, respectively.

FIG. 2 shows the DNA sequence of UL32 gene (SEQ ID NO:1).

FIG. 3 shows the amino acid sequence of the protein encoded by the UL32 gene (SEQ ID NO:2).

Lane 1: CEF cells infected with recFPV/MD-gB/UL32 with monoclonal antibody 1AN86 specific for MD gB; lane 2: uninfected CEF cells with monoclonal antibody 1AN86; lane 3: CEF cells infected with recFPV/MD-gB/UL32 with monoclonal antibody for gp82; lane 4: CEF cells infected with the GA strain of MDV with monoclonal antibody for gp82.

Figure 9A:
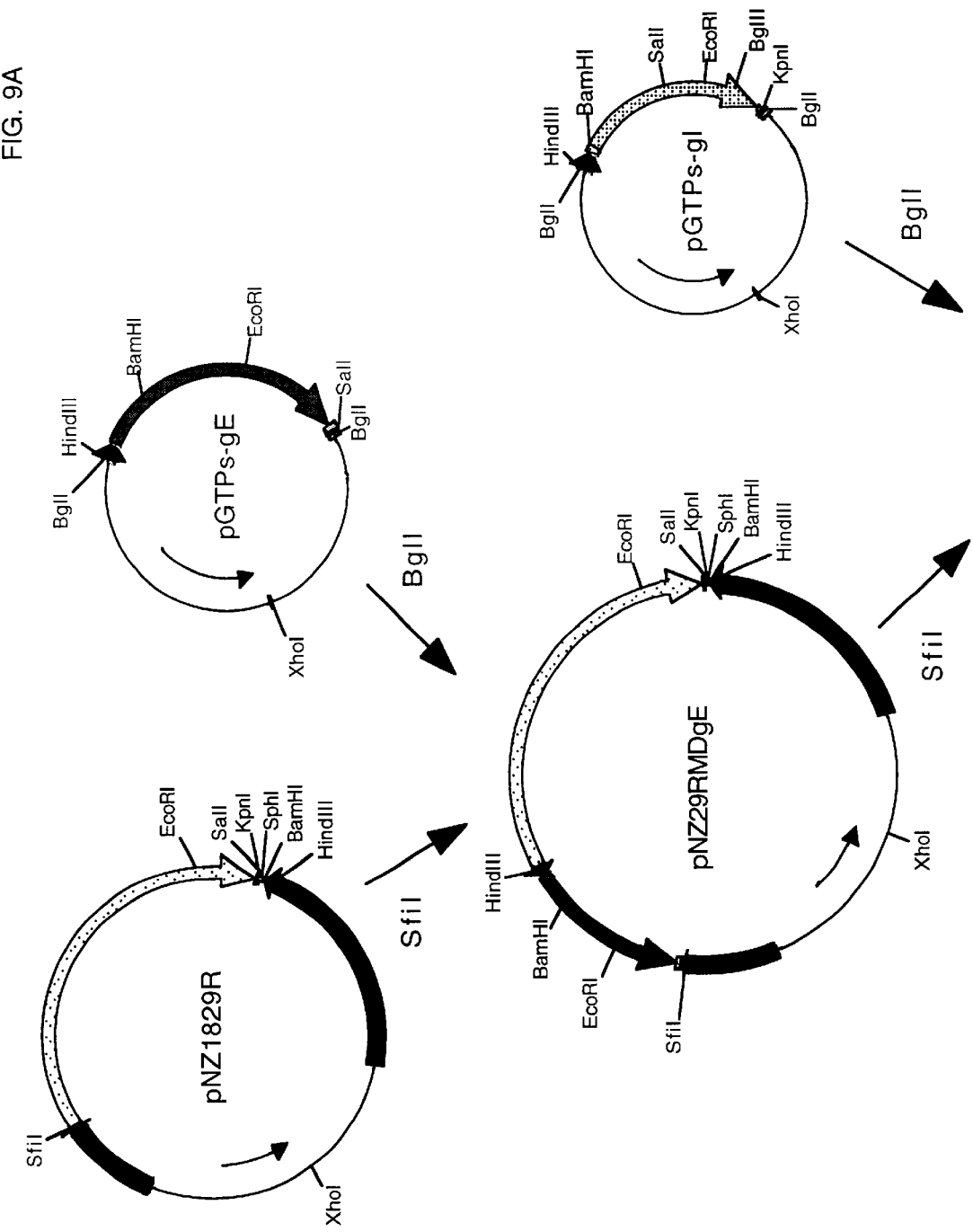
Figure 9B:
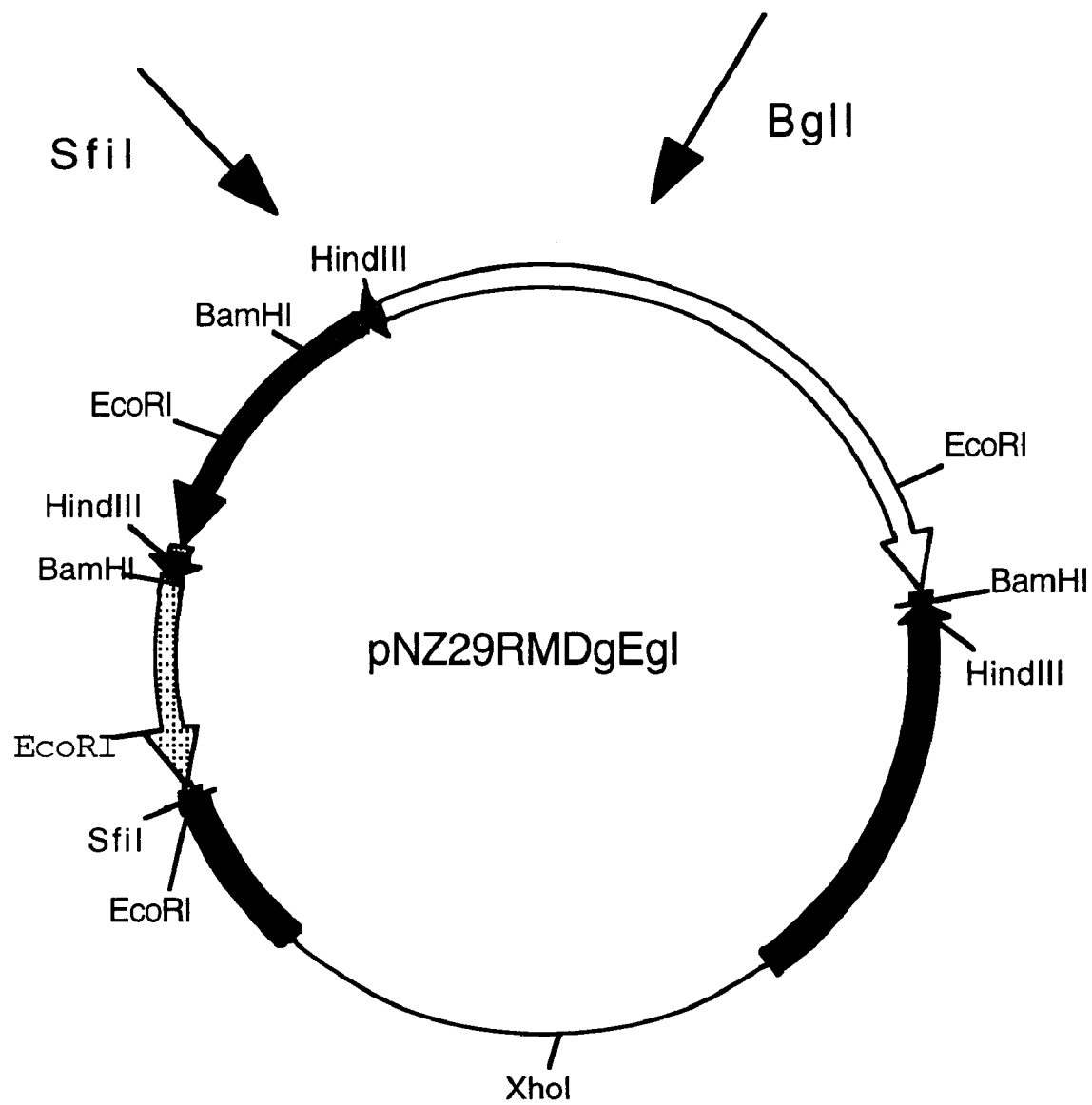
Figure 10A:
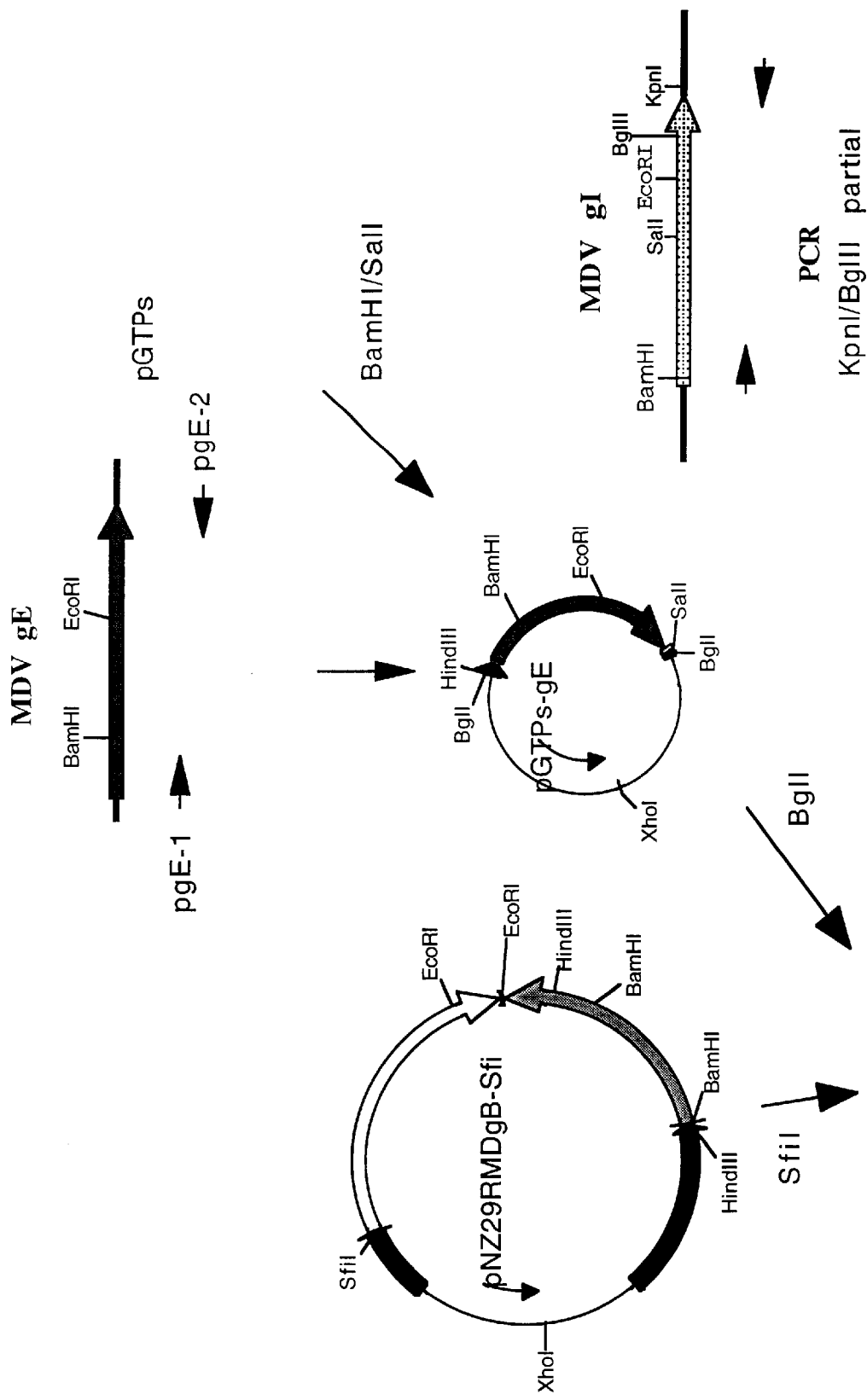
Figure 10B:
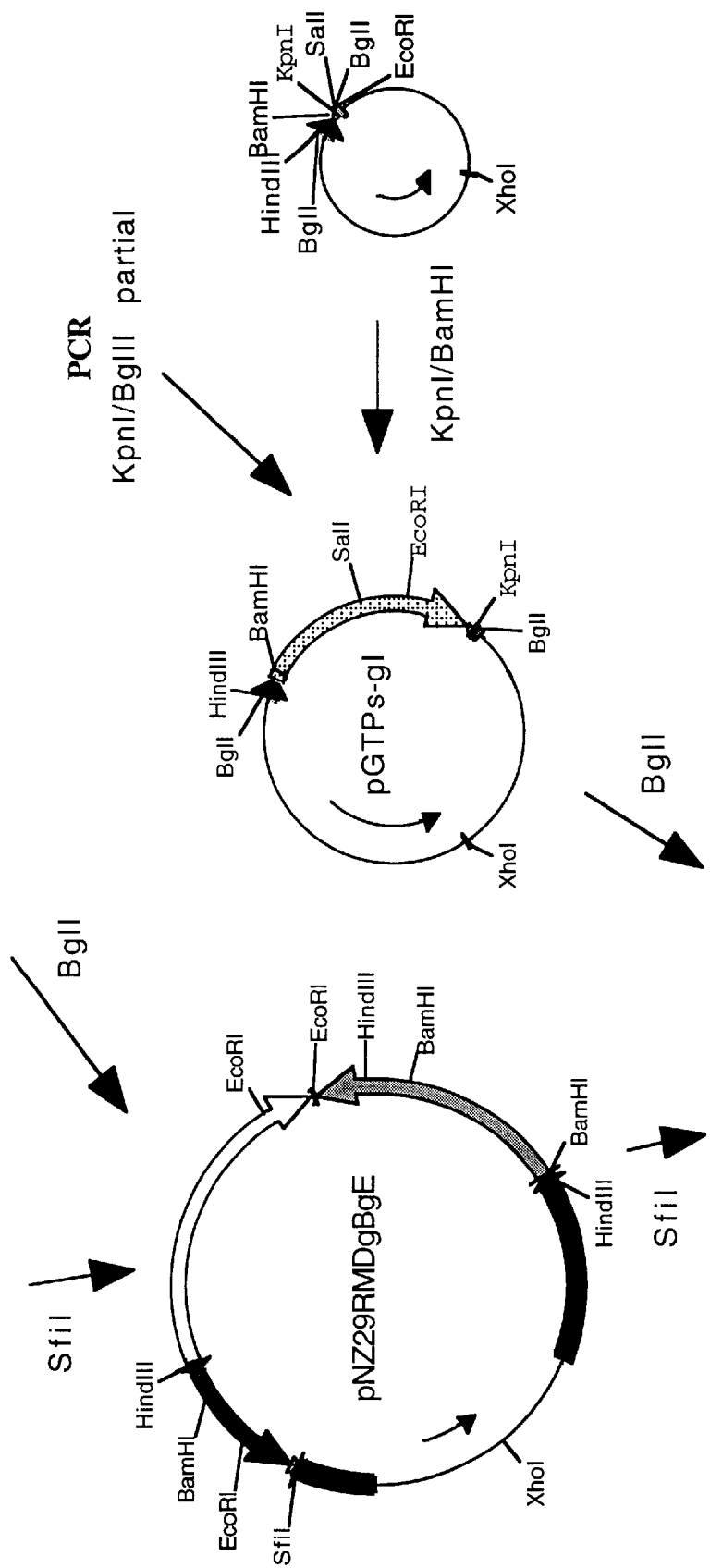
Figure 10C:
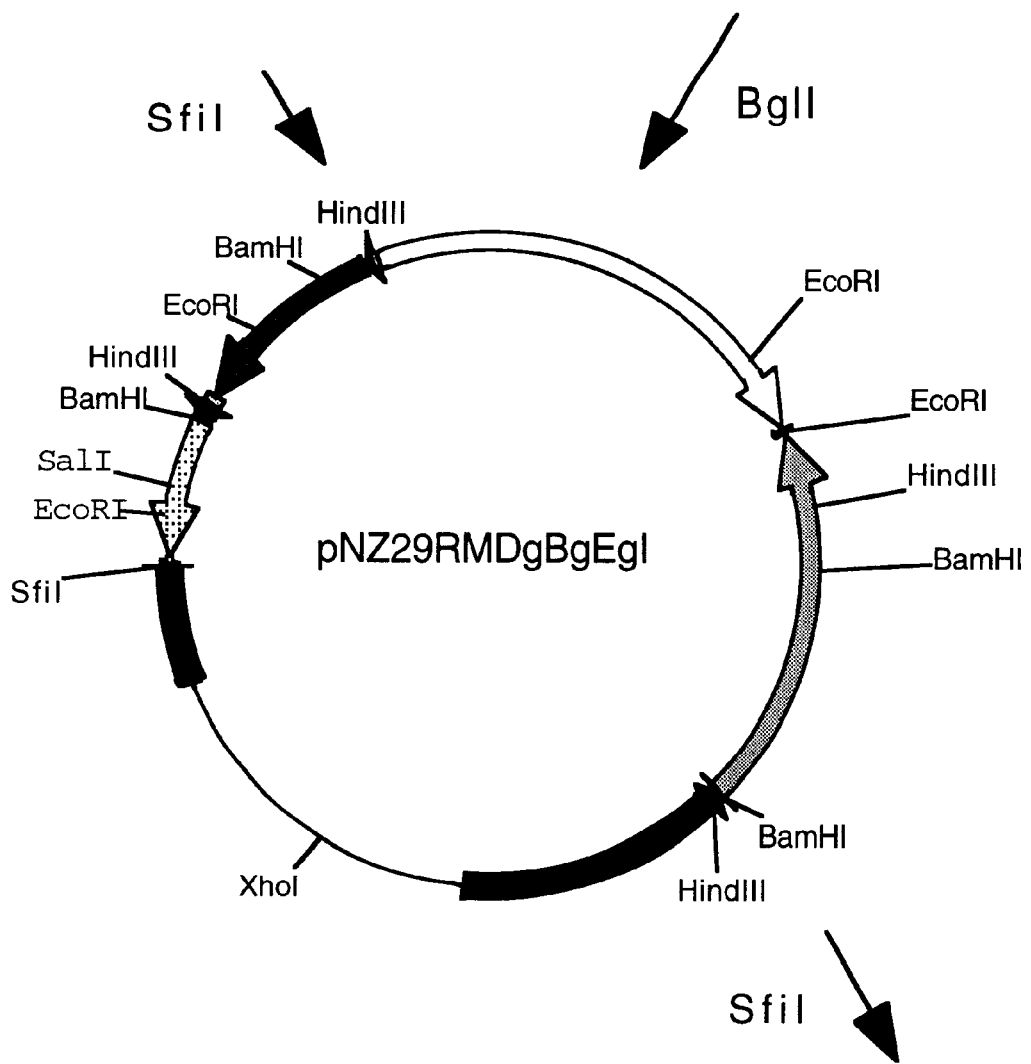
Figure 10D:
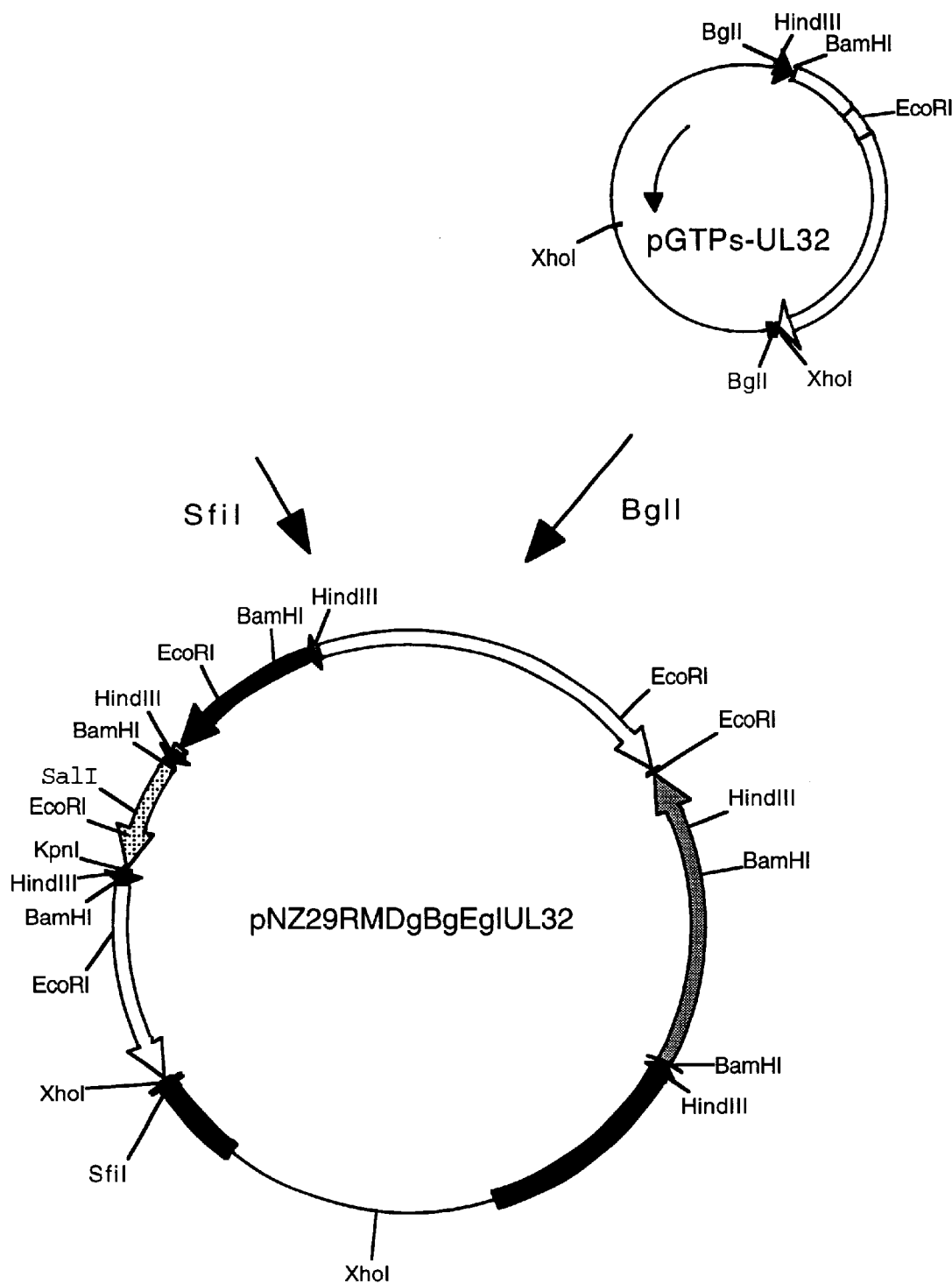

FIGS. 9A–9B show the construction of the plasmids pNZ29RMDgE and pNZ29RMDgEgI.

FIGS. 10A–10D show the construction of the plasmids pNZ29RMDgBgE, pNZ29RMDgBgEgI and pNZ29RMDgBgEgIUL32.

DETAILED DESCRIPTION OF THE INVENTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

The contents of each of the references cited herein are herein incorporated by reference in their entirety.

The UL32 Gene and the Polypeptide Encoded Thereby

The UL32 gene of the present invention is a 1926 base long DNA obtained from Marek's disease virus comprising the sequence from nucleotides 1–1926 of SEQ ID NO:1, or a DNA sequence originating from MDV substantially equal to the 1926 base long DNA that retains the functional activity thereof. Although the DNA sequence shown in SEQ ID NO:1 is that form obtained from strain GA, the present invention is not limited to the gene originating from the GA strain alone.

Biologically Functionally Equivalent DNA Fragments

The nucleic acid sequences disclosed herein, or their biologically functional equivalents, can be used in accordance with the present invention. The phrase "biologically functional equivalents," as used herein, denotes nucleic acid sequences exhibiting the same or similar biological activity/immunoprotective activity as the particular nucleic acid sequences described herein, i.e., when introduced into viral hosts in a functionally operable manner so that they are expressed, they elicit a protective immune response.

For example, the nucleic acid sequences described herein can be altered by base substitutions, insertions, additions, or deletions to produce biologically functionally equivalent nucleic acids that encode proteins conferring immunity to MDV in vivo. In addition, due to the degeneracy of the genetic code, other DNA sequences that encode substantially the same amino acid sequences as described herein and confer immunity to MDV in vivo can be used in the practice of the present invention. These include, but are not limited to, nucleotide sequences comprising all or portions of the viral DNAs described herein or the corresponding mRNAs or cDNAs that are altered by the substitution of different codons that encode a physiologically functionally equivalent amino acid residue within the protein sequence, thus producing a silent change. Similarly, the proteins conferring immunity to MDV, or derivatives thereof, encoded by the present invention include, but are not limited to, those containing all of the amino acid sequences encoded by the DNA sequences substantially as described herein, including altered sequences in which functionally equivalent amino acid residues are substituted for residues within the sequence, resulting in a silent change. For example, one or more amino acid residues within the sequence can be substituted with another amino acid of similar polarity which acts as a functional equivalent, resulting in a silent alteration. Substitutes for an amino acid within the sequence may be selected from other members of the class to which the amino acid belongs. For example, fungible nonpolar (hydrophobic) amino acids include alanine, leucine, isoleucine, valine, proline, phenylalanine, tryptophan, and methionine. Fungible polar neutral amino acids include glycine, serine, threonine, cysteine, tyrosine, asparagine, and glutamine. Fungible positively charged (basic) amino acids include arginine, lysine, and histidine. The negatively charged (acidic) amino acids include aspartic acid and glutamic acid.

The variants of the genomic DNAs, the corresponding mRNAs or cDNAs, and proteins contemplated herein should possess more than 75% homology, preferably more than 85% homology, and most preferably more than 95% homology, to the naturally occurring viral DNAs, the corresponding mRNAs or cDNAs, and proteins discussed herein.

Also included within the scope of the present invention are gp82 protein fragments, which are the expression products of the UL32 gene, or derivatives thereof that are differentially modified during or after translation, e.g., by glycosylation, proteolytic cleavage, etc.

In the present invention, DNAs substantially biologically functionally equivalent to the UL32 gene possessing the nucleotide sequence 1–1926 of the nucleotide sequence shown in SEQ ID NO:1 are defined either as DNAs originating from MDV, the length of which has been altered by either natural or artificial mutations such as partial nucleotide deletion, insertion, addition, or the like, so that when the entire length of SEQ ID NO:1 is 100%, the resulting sequence has an approximate length of 60–120% of that of SEQ ID NO:1, preferably 80–110%, or a gene partially (herein partially means usually 20% or less, preferably 10% or less, and more preferably 5% or less of the entire length) replaced and altered by either natural or artificial mutations so that the nucleotide sequence codes for different amino acids, but wherein the resulting protein retains the immunoprotective effect of the naturally occurring protein. The mutated DNA created in this manner must usually encode a protein having 75% or greater, preferably 85% or greater, and more preferably 95% or greater, similarity to the amino acid sequence of the UL32 protein (SEQ ID NO:2) encoded by the nucleotide sequence of SEQ ID NO:1.

In the present invention, similarity means that which is measured by the method of Gonnet et al. (*Science* 256:1443–1445 (1992)).

In the present invention, the methods employed to create artificial mutations are not specifically limited, and therefore such mutations can be produced by any of the standard means. For example, the UL32 gene obtained from a field strain MDV can be reinserted after treatment with appropriate restriction enzymes and insertion (or deletion) of appropriate DNA fragments so that the proper amino acid reading frame is preserved. In addition, the in vitro mutagenesis methods described by Frits Eckstein et al., (*Nucleic Acid Research* 10:6487–6497 (1982)), Osuna et al. (*Critical Reviews in Microbiology* 20:107–116 (1994), and other methods can be used to alter a nucleotide sequence so that part of the amino acid sequence is translated into different amino acids. Biologically functional equivalents to the nucleic acid fragments disclosed herein can be selected for using the techniques described in Examples 3–8, below.

The DNAs described above that have been mutated by the above-mentioned methods and other methods are considered to possess biological function substantially equal to that of the UL32 gene of the present invention. The UL32 gene of the present invention can function to suppress symptoms of MDV infection in chickens when inoculated as a recombinant avipoxvirus carrying the UL32 gene. If the effect of a particular mutated DNA differs from the effect of the UL32 gene derived from MDV strain GA ±20% or less, such DNA is considered to possess a function substantially equal to that of the UL32 gene of the present invention.

The aforementioned gene of the present invention is presumably considered to exist in the genome of all MDV serotypes. Therefore, the gene of the present invention can be obtained from any MDV strain by conventional methods, for example Southern hybridization using probes arbitrarily selected from the nucleotide sequence shown in SEQ ID NO:1.

Sources of the UL32 gene include the serotype 1 strains such as GA, RB1B, CVI988, 584A and Md5; serotype 2 strains such as SB-1 and 301B/1; and serotype 3 strains such as FC126, YT-7 and H2. Among these, serotype 1 is preferable.

The polypeptides of the present invention possess the amino acid sequence encoded by the aforementioned DNA sequences, and such polypeptides can be easily produced and purified by the usual methods using recombinant viruses as described below.

Recombinant Viruses

The recombinant viruses of the present invention harbor the UL32 gene of the present invention. In addition, they may also harbor antigen genes other than the UL32 gene. An example of the preparation of such recombinant viruses is as follows.

A plasmid which contains a nonessential region of the parent virus is constructed. The UL32 gene is placed under control of a promoter that functions in the parent virus. A plasmid vector is obtained by inserting the UL32 construct into the nonessential region of the above plasmid. In the next step, homologous recombination is induced by introducing the plasmid vector into cells infected with the parent virus. Recombinant viruses are obtained by subjecting the resulting viruses to selection and purification.

Parent Virus

In the present invention, "parent virus" means a virus in which the UL32 gene and other genes can be inserted. This can be any kind of virus. For example, for use as a vaccine, a virus that can infect the birds to be vaccinated is preferable. Examples of such viruses include viruses generally used for recombination: poxviruses, including orthopoxviruses such as racoon poxvirus and vaccinia virus, and avipoxviruses (APV) such as pigeon poxvirus, fowl poxvirus, canary poxvirus, quail poxvirus, and turkey poxvirus; herpesviruses such as turkey herpesvirus (HVT) and infectious laryngotracheitis virus (ILTV); adenoviruses; and influenza viruses.

Vaccinia viruses include the Copenhagen strain and the WR strain. Avipoxviruses include viruses that can replicate in poultry cells such as those of chicken, turkey, and duck, for example, FPV, pigeon poxvirus, canary poxvirus, turkey poxvirus, and quail poxvirus. FPV strains include ATCC VR-251, ATCC VR-250, ATCC VR-229, ATCC VR-249, ATCC VR-288, Nishigahara, Shisui, and the CEVA vaccine strain. Among viruses derived from the CEVA vaccine strain, there are strains that form large plaques upon infection of chick embryo fibroblast cells (CEF), and therefore belong to the narrow definition of FPV. Other viruses like the NP strain (derived from the Nakano strain of chicken-fetus-adapted pigeon poxvirus) are closely related FPV of the narrow definition, and are used to produce live chicken poxvirus vaccines. Herpesviruses include HVT such as the FC126 and H2 strains, which can be obtained from Nippon Institute for Biological Science (Nisseiken Co., Ltd.), and the YT-7 strain, which can be obtained from the Chemo-Sero-Therapeutic Research Institute (Kagaku Oyobi Kesseiryoho Kenkyusho); ILTV such as strains like C7 and CE, which are currently used as anti-ILTV vaccines, and the NS-175 strain.

Among these viruses, avipoxviruses and avian herpesviruses are especially preferable.

Nonessential Regions

The nonessential region used in the present invention is defined as a region that is not essential for replication of the parent virus. For example, if the parent virus is a vaccinia virus, the TK gene region and the HA gene region are nonessential regions. If the parent virus is an avipoxvirus, the TK gene region of turkeypox, fowlpox, pigeonpox, and quailpox viruses and the region described in Japanese Patent Application Laid-open (Kokai) No. 168279/1989 can be used. In addition, the regions which homologously recombine with these regions are examples of nonessential regions. The DNA fragments of the APV-NP strain are described in the above Japanese Patent Application Laid-open (Kokai) No. 168279/1989 (EcoRI fragment (7.3 kbp), EcoRI-HindIII fragment (approximately 5.0 kbp), BamHI fragment (approximately 4.0 kbp), and HindIII fragment (approximately 5.2 kbp). If the parent virus is a herpesvirus, nonessential regions include the TK gene region, the region homologous to the gC gene of herpes simplex virus (gC homologue), and the unique short regions such as the Us2 homologue of herpes simplex virus.

Vectors Containing Nonessential Regions

Vectors containing nonessential regions are used in the construction of vectors for recombination described below. Such vectors can be constructed by the usual methods, for example, by inserting the nonessential regions described above into vectors treated with appropriate restriction enzymes. Vectors which can be used in the construction include plasmids such as pBR322, pBR325, pUC7, pUC8, pUC18, and the like; phages such as $\lambda$ and M13, and the like; and cosmids such as pHC79 and the like.

Transfer Vectors for Recombination

Transfer vectors for recombination used in the present invention contain nonessential regions into which is inserted the UL32 gene, other antigen genes which may be optionally employed, and promoters which control these genes. Such vectors can be constructed by inserting into the viral non-essential regions of the above-mentioned vectors containing nonessential regions the UL32 gene of the present invention as well as antigen genes selected as needed with promoters which control these genes at the 5' upstream position of each gene.

Furthermore, in order to facilitate efficient purification of recombinant viruses, marker genes such as the *E. coli* lacZ gene may be inserted with promoters described below which control such genes.

Antigen Genes

In the present invention, an antigen gene or genes in addition to the UL32 gene can be employed. Such antigen genes are defined as genes that encode antigen proteins expressed by poultry pathogens (bacteria, viruses, etc.), and that can also be expressed as antigenic proteins by the process of transcription and translation when inserted into a parent virus. Preferable examples of antigen-protein encoding DNAs (antigen genes) include the genes encoding the MDV glycoproteins gB, gI, gE, etc. (gB: Ross et al. *J. Gen Virol.* 70:1989–1804 (1988); gI and gE: Velicer et al., (U.S. Pat. No. 5,252,716); the gene encoding NDV HN (Miller et al. *J. Gen. Virol.* 67:1917–1927 (1986)), the gene encoding the F protein (McGinnes et al. *Virus Res.* 5:343–356 (1986)), the gene encoding the structural protein VP2 of infectious bursal disease virus (Bayliss et al. *J. Gen. Virol.* 71:1303–1312 (1990)), and other genes encoding antigens involved in protection against infection.

Any gE gene or gI gene is usable in the present invention so long as the gE gene or gI gene is derived from the genome of a Marek's disease virus.

Said gE gene or said gI gene is not necessarily a gene having the complete sequence of a gE or gI gene. If a gene encodes a protein having substantially the same function as a protein encoded by a gE or gI gene, such a gene is also usable in the present invention.

In the present invention, the phrase "substantially biologically functionally equivalent gene to said gE gene or said gI gene" denotes a gene that has an approximate length of about 80–120%, preferably about 90–110%, of the length of said gE gene or said gI gene. The length is altered by either natural or artificial mutations such as nucleotide deletions, insertions, addition of new sequence, or the like, wherein the entire length of said gE gene or said gI gene is taken as 100%. A substantially biologically functionally equivalent gene is also a gene partially replaced and altered by either natural or artificial mutations so that the nucleotide sequence codes for different amino acids, but wherein the resulting protein retains the immunoprotective effect of the naturally occurring protein. Herein "partially" means 20% or less, preferably 10% or less, and more preferably 5% or less of the entire sequence of the gene is altered. The mutated DNA created in this manner must usually encode a protein having 80% or greater, preferably 90% or more, and more preferably 95% or greater, homology to the amino sequence of the protein naturally encoded by said gE or said gI gene. In this respect, the term "homology" means identity as measured using DNA sequence analysis software, such as DNASIS, available from Takara Shuzo KK.

In the present invention, the methods employed to create artificial mutations are not specifically limited, and therefore such mutations can be produced by any of the standard means. For example, the naturally occurring gE gene obtained from a field strain of MDV can be reinserted into a vector after treatment with appropriate restriction enzymes and insertion (or deletion) of appropriate DNA fragments so that the proper amino acid reading frame is preserved. In addition, the in vitro mutagenesis methods described by Frits Eckstein et al., (*Nucleic Acid Research* 10:6487–6497 (1982)), and other methods can be used to alter a nucleotide sequence so that part of the amino acid sequence is translated into amino acids different from the amino acids normally found in the protein.

The proteins encoded by the DNAs described above that have been mutated by the above-mentioned methods and other methods are considered to possess biological function substantially equal to that of the protein encoded by the naturally occurring gE or gI. The phrase "the function of the naturally occurring gE or gI" means a function of inhibiting the immune response derived from complement-dependent or antibody-dependent cell damage as a corollary of having a physiological activity that a conjugate gI-gE or gE itself bonds to $F_c$ portion of IgG. The phrase "function substantially equal to that of the naturally occurring gE or gI" means an activity equal to about 1.5 times or more, preferably about 2.0 times or more of the protection effect observed in the group of animals vaccinated with a recombinant avipox virus into which an antigen gene such as a UL32 gene, a gE gene and, optionally, a gI gene have been incorporated without making gE and gI expressed. The activity is determined by using animals retaining about 50% of the transfer antibody just after the birth with said recombinant virus. The vaccinated animals are then infected with a virulent strain of MDV when the transfer antibody has become substantially lost (to about 10% or less of the level found in the newborn animals). "Transfer antibody" is antibody passed from the mother to the newborn during egg development.

As an exemplified gene for said gE derived from Marek's disease virus or a gene substantially equalivalent thereto, one may give a DNA encoding the amino acid sequence derived from Marek's disease virus type I strain GA (SEQ ID NO:29). As an example of said gI gene or an equivalent thereof one may give a DNA encoding the amino acid sequence derived from Marek's disease virus type I strain GA (SEQ ID NO:28).

In the present invention, the gE gene can provide an effect as a vaccine which is seldom affected by the transfer antibody even if the gE gene is used singly. However, more effective protection can be attained if a recombinant virus into which the gI gene has been incorporated together with the gE gene is used.

There are no specific limitations with respect to the order of the linkage between the gE gene, the gI and an antigen gene which will be described hereinafter in detail as far as respective genes are linked in such a manner that each of said gE, said gI and said antigen gene are substantially expressed. That is, a possible linkage would be gE gene—GI gene—antigen gene; gI gene—gE gene—antigen gene; gE gene—antigen gene—gI gene; gI gene—antigen gene—gE gene; antigen gene—gE gene—gI gene or antigen gene—gI gene—gE gene; ordered from the 5' end. Alternatively the gE gene can be linked after the gI gene, that is, at the 3'-position and the antigen gene can be linked to the resultant gI-gE construct at the 3'- or 5'-position.

There are no specific limitations as to the position for linking a useful marker gene.

Neither are there specific limitations as to the methods for linking those genes and any conventional method such as the one in which a suitable linker is employed for the linkage or the one in which a recombinant vector is directly produced by homologous recombination using respective gene-containing vectors.

Promoters

The promoters used in the present invention are not limited to particular promoters, and can be any promoters as far as they exhibit promoter activity in hosts infected with recombinant viruses. They may be natural virus promoters, modified natural virus promoters, or synthetic promoters.

Natural virus promoters include, in cases wherein the parent virus is a poxvirus such as VV, APV, and the like, the promoter of the vaccinia virus gene that encodes the 7.5 KDa polypeptide, the promoter of the vaccinia virus gene that encodes the 11 KDa polypeptide, and the promoter of the vaccinia virus gene that encodes thymidine kinase. These promoters can be modified by alteration, addition, deletion, and gain or loss of nucleotides so long as they exhibit promoter activity.

Examples of synthetic promoters include the synthetic promoter which contains both early and late promoter sequences (A. J. Davidson et al. *J. Mol. Biol.* 215:749–769 and 771–781 (1989)), and derivatives thereof that have been partially modified by deletion and/or alteration of nucleotides, but still retain their promoter activity. An example is a sequence having the nucleotide sequence: 5'-TTTTTTTTTTTTTTTTTTTGGCATATAAATAATA AATACAATAATTAATTA CGCGTAAAAAT-TGAAAAACTATTCTAATTTATTGC ACTC-3' (SEQ ID NO:3). This synthetic promoter and its modified forms contain a long stretch of T bases at their 5' end. It has been determined that this all T region should preferably contain 15–40, more preferably 18–30, T bases for promoter activity and expression of antigen genes.

It is possible to insert promoters in a manner such that each of the UL32, additional antigen, and marker genes is controlled individually. In such a construct, the promoters connected to the genes need not be the same promoters.

Methods of Constructing Recombinant Viruses

There are no specific limitations with respect to the method for constructing recombinant viruses. Such constructs can be produced by conventional methods. For example, recombinant viruses can be obtained through induction of homologous recombination between a vector and the virus genome present in infected cells by introducing a recombinant vector containing the UL32, additional antigen, and other genes into cells that have been infected with a parent virus. Recombinant viruses obtained in this manner can be purified by infecting host cells cultured in a medium such as Eagle's MEM, and by selecting candidate strains by the use of the hybridization method with the inserted antigen gene as a probe and by expression of the marker gene inserted with the antigen gene. Purified candidate strains thus obtained can be confirmed as desired recombinant viruses by methods such as immunoassays using an antibody against the polypeptide encoded by the inserted antigen gene. For example, APV containing the lacZ gene as the marker gene expresses β-galactosidase, and therefore forms blue plaques in the presence of one of its substrates, Bluogal (manufactured by GIBCO-BRL), thus enabling selection and purification.

Host cells are not limited to particular cells, and can be any cells which the virus in use can infect and replicate in, for example, chicken embryo fibroblast (CEF) cells and chicken embryo chorioallantoic membrane cells in the case of FPV.

Poultry Vaccines

The vaccines of the present invention include vaccines containing as an active ingredient the UL32 gene, or a recombinant vector or vectors which contain the UL32 gene (vaccine I), vaccines containing as an active ingredient recombinant virus or viruses that contain the UL32 gene as well as other antigen genes inserted as needed (vaccine II), vaccines containing other vaccine ingredients in addition to vaccine II (vaccine III), and vaccines containing as an active ingredient the polypeptide encoded by the UL32 gene (vaccine IV).

Vaccines of the present invention are administered in effective amounts as described below.

Vaccines Containing as an Active Ingredient the UL32 Gene, or a Recombinant Vector or Vectors Which Contain the UL32 Gene (Vaccine I)

Recombinant vectors used herein can be any vectors that contain the UL32 gene of the present invention with an inserted promoter sequence that is functional in eukaryotic cells, but preferably plasmid vectors that can be easily propagated in E. coli. The promoter functional in eukaryotic cells can be of either cellular origin, such as the actin gene promoter, or viral origin, such as a cytomegalovirus promoter or a retrovirus LTR.

Vaccines in the form of purified DNA can be administered by intramuscular, intravenous, intraperitoneal, or subcutaneous injection, but intramuscular injection is most preferred. Direct DNA administration can be accomplished with a syringe, but more preferably by a so-called Gene-gun. DNA should be administered in a dose that can achieve sufficient immunological induction, usually 10–300 μg divided into 2 to 4 inoculations. If a Gene-gun is used, the DNA dosage can be reduced to one-tenth the above dose or less.

Vaccines Containing as an Active Ingredient Recombinant Virus or Viruses Which Contain the UL32 Gene as Well as Other Antigen Genes Inserted as Needed (Vaccine II)

Vaccine II is composed of one or more recombinant viruses selected from (i) a recombinant virus carrying the UL32 gene of the present invention, (ii) a recombinant virus carrying the UL32 gene as well as another antigen gene(s), and (iii) a mixture thereof. The recombinant virus (ii) is superior to the recombinant virus (i). Said recombinant virus can be used singly or in combination with 2–3 other recombinant viruses of the present invention. Also, in addition to recombinant viruses, pharmacologically inactive materials such as physiological saline and stabilizing agents can be added.

There are no specific limitations on the method for preparing vaccine II of the present invention. For example, cells susceptible to recombinant viruses of the present invention can be infected with one of the recombinant viruses of the present invention and cultured until the recombinant virus propagates in these cells. Cells are then collected and disrupted. Centrifugation of the disrupted cells separates the high titer supernatant from the precipitate. The supernatant which is essentially free of host cells and contains cell culture medium and the recombinant virus can be used as a vaccine of the present invention. The vaccine can be diluted prior to use with a pharmacologically acceptable diluent such as physiological saline. The supernatant can also be used as a freeze-dried vaccine after lyophilization.

If one of the vaccines of the present invention is to be used as a vaccine for chickens, administration thereof can be achieved by any method by which the recombinant virus in the vaccine can infect poultry and induce protective immunity in the infected birds. For example, inoculation can be performed by stabbing the wing web or scratching the skin. Subcutaneous injection using a needle or other tools can also be used for inoculation. Oral administration can be achieved by suspending the vaccine in poultry drinking water or mixing the vaccine in solid feed. In addition, among other methods, inhalation of the vaccine in the form of an aerosol or spray, intravenous injection, intramuscular injection, and intraperitoneal injection can also be used.

The dosage for chickens is usually 10–$10^6$ plaque forming units (PFU), preferably $10^2$–$10^5$ PFU, per bird. For injection, vaccines containing the above titer should be diluted with a pharmacologically acceptable liquid such as physiological saline to a final volume of approximately 0.1 ml or 0.01 ml in the case of wing web administration.

The vaccines of the present invention can be stored and used under normal conditions. For example, lyophilized recombinant viruses of the present invention can be stored in a refrigerator (0–4° C.), or even at room temperature (20–22° C.) for a short period. Virus suspensions can be stored frozen at −20° C. to −70° C.

Vaccines Containing Other Vaccine Ingredients in Addition to Vaccine II (Vaccine III)

Other vaccine ingredients in vaccine III include, for example, antigen genes, recombinant viruses which carry one or more antigen genes but not the UL32 gene, inactivated vaccines, and component vaccines. Examples of other vaccine ingredients defined above include recombinant APV which does not contain the UL32 gene, Marek's disease vaccines (FC126 strain of HVT, strain CVI988 of serotype 1 MDV, SB-1 and 301B/1 strains of serotype 2 MDV), ILTV vaccines, and avian encephalomyelitis vaccines. Vaccine III can be produced by mixing these and vaccine II described above by a pharmacologically acceptable method. In fact, mixing with a commercially available anti-Marek's disease vaccine, HVT vaccine, proves to be highly effective.

In such cases, the dosage of each vaccine can be set arbitrarily. For example, the dosage for vaccine II is set at 1/10 to 1 times the dosage described above, i.e., for chickens, $10^0$ to $10^6$, preferably $10^1$ to $10^5$, PFU per bird. Similarly, other vaccines should also be used at about 1/10 to 1 times the usual dosage.

For storage of vaccine III, the characteristics of each ingredient should be taken into consideration. All the ingredients can be stored together or separately.

Also, it should be pointed out that the most distinctive feature of vaccine III is the use of vaccine II in combination with other ingredients. Therefore, simultaneous administration of vaccine II and other vaccine ingredients as well as administration of a mixture of vaccine II and other ingredients is expected to produce excellent effects. "Simultaneous" herein means within 7 days, preferably 3 days, before or after the administration of vaccine II.

Vaccines Containing as an Active Ingredient the Polypeptide Encoded by the UL32 Gene (Vaccine IV)

The polypeptide encoded by the UL32 gene can be prepared by either infecting susceptible host cells with the plasmid vectors or virus vectors mentioned above in the descriptions of vaccines I and II, or by expressing the UL32 gene in expression systems such as *E. coli,* yeast, and baculovirus. The polypeptide can then be used as a vaccine with a common adjuvant such as Alum and FCA. of course, pharmacologically acceptable vehicles such as physiological saline and stabilizing agents can be added to the vaccine.

The present invention will be described in detail in the following Examples. However, it should be understood that the Examples presented below are merely illustrative, and not limiting of the present invention.

EXAMPLE 1

Cloning and Sequencing of the UL32 Gene

The BamHI-E fragment of MDV DNA in pACYC184 (Fukuchi et al. *J. Virol.* 51:102–109 (1984)) was cloned into the BamHI site of pUC18 for sequencing, and various subclones were prepared from this fragment using appropriate restriction enzymes. The fragment was treated with exonuclease III followed by mung bean nuclease to make sets of deletion mutants when necessary. DNA sequencing was performed on double stranded plasmid by the dideoxy chain termination method using α-$^{35}$S) DATP (NEN) and the TAQuence version 2.0 DNA Sequencing Kit (United States Biochemical Corporation) as suggested by the manufacturer. The ORF of UL32 has a size of 1,926 bps and is leftward, and contains an average base composition of 27.6% A, 24.2% G, 19.8% C, and 28.3% T.

The DNA sequence upstream and downstream of UL32 was analyzed for putative transcriptional control elements. A consensus "TATA" box (5'-TATTAA-3'), characteristic of many eucaroytic and also herpesviral promoters, is located −151 nucleotides upstream from the proposed initiation codon. The sequence 5'-CCGAATGG-3', which resides 87 nucleotides upstream from the "TATA" box, exhibits similarities to the "CAT" box consensus sequence (5'-GGYTCAATCT-3') (SEQ ID NO:4). A possible SP-1 binding element (CCGCCC) is located at position −337 nucleotides upstream from the start codon.

Regarding 3' elements of UL32, there is no suitable poly A sequence (AATAAA or ATTAAA) downstream from the ORF. However, there exist a "CAT" box (5'-GACCAATCC-3') and a "TATA" box (5'-TATAAA-3') at the C-terminal of UL32.

EXAMPLE 2

Identification of the UL32 Gene Product

The polypeptide predicted from the nucleotide sequence (SEQ ID NO:1 and FIG. 1) comprises 641 amino acids with a calculated molecular weight of 71.5 KDa. The amino acid sequence is shown in FIG. 2 and SEQ ID NO:2. The polypeptide is far from a typical classical membrane protein. There is no signal sequence, and it has only 4 potential domains (amino acid residues 86–104; 124–140; 464–482; and 586–597) that may interact with or span the membrane. In this polypeptide, there are two potential N-linked glycosylation sites (amino acid resides 47 and 242).

EXAMPLE 3

Construction of pGTPs, the Plasmid for Antigen Gone Insertion

Figure 4:
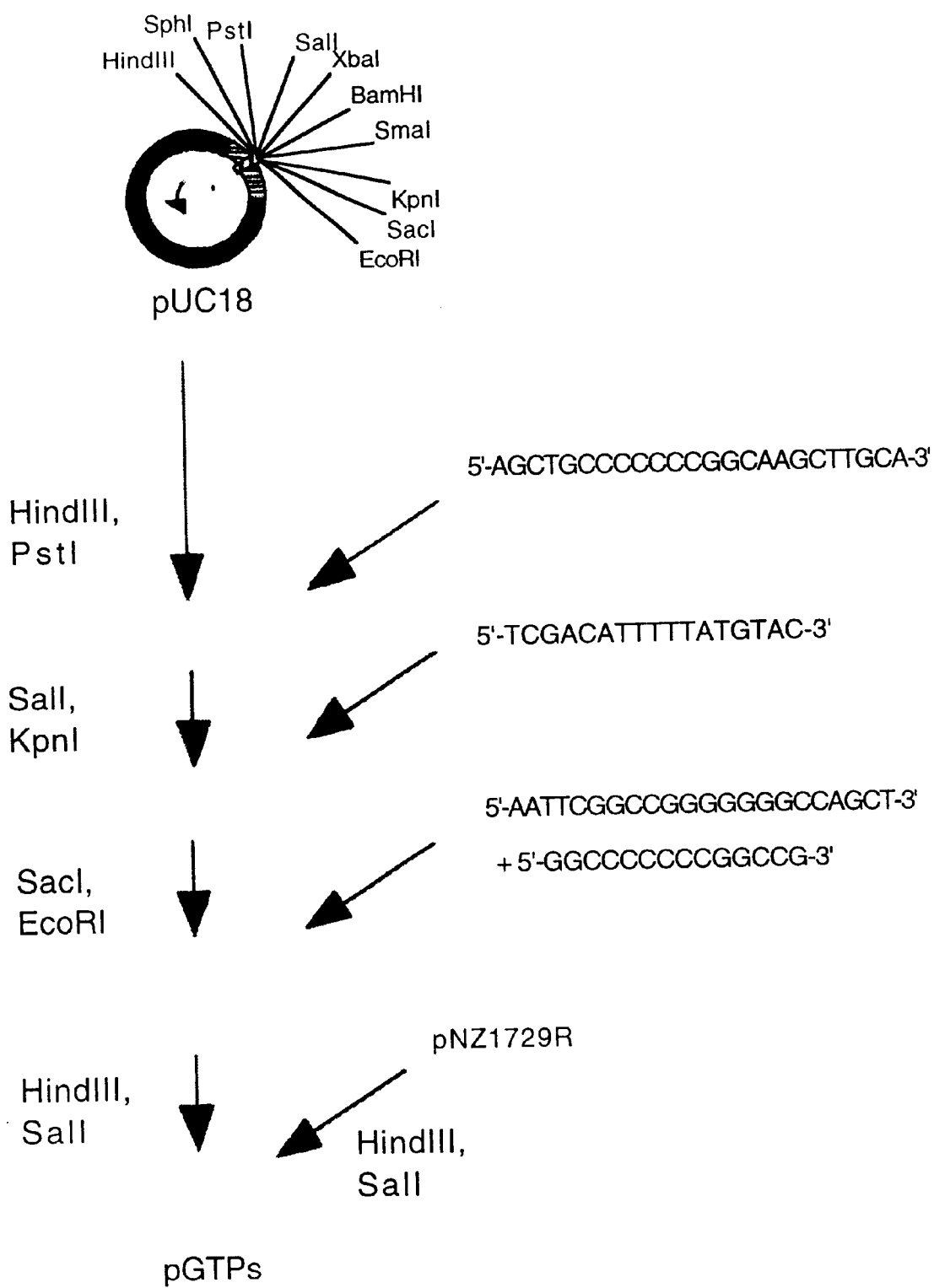
FIG. 4 shows the construction of plasmid vector pGTPs.
Figure 5A:
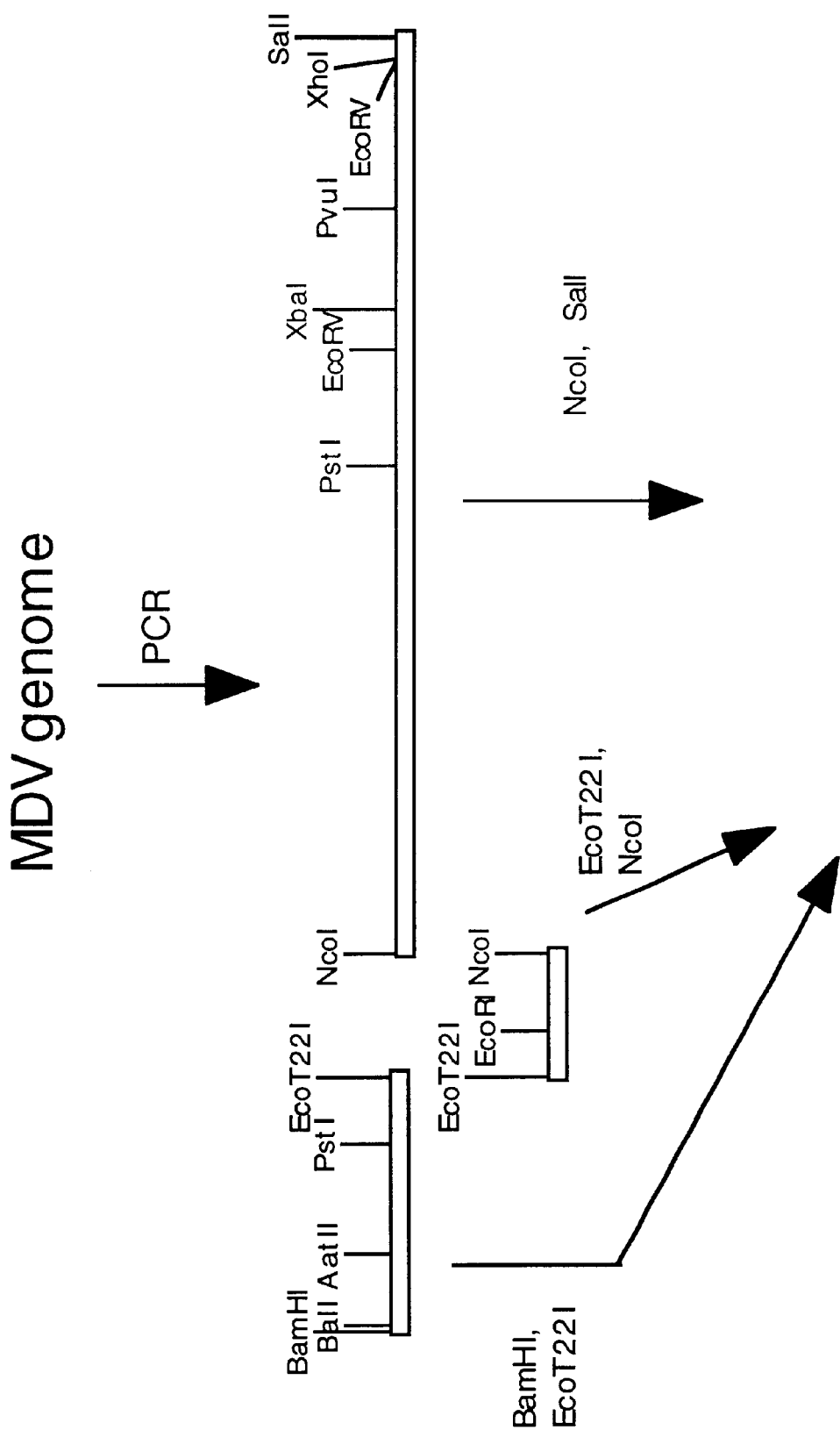
FIGS. 5A–5D show the construction of transfer vectors pNZ29RMDUL32 and pNZ29RMDgBUL32.
Figure 5B:
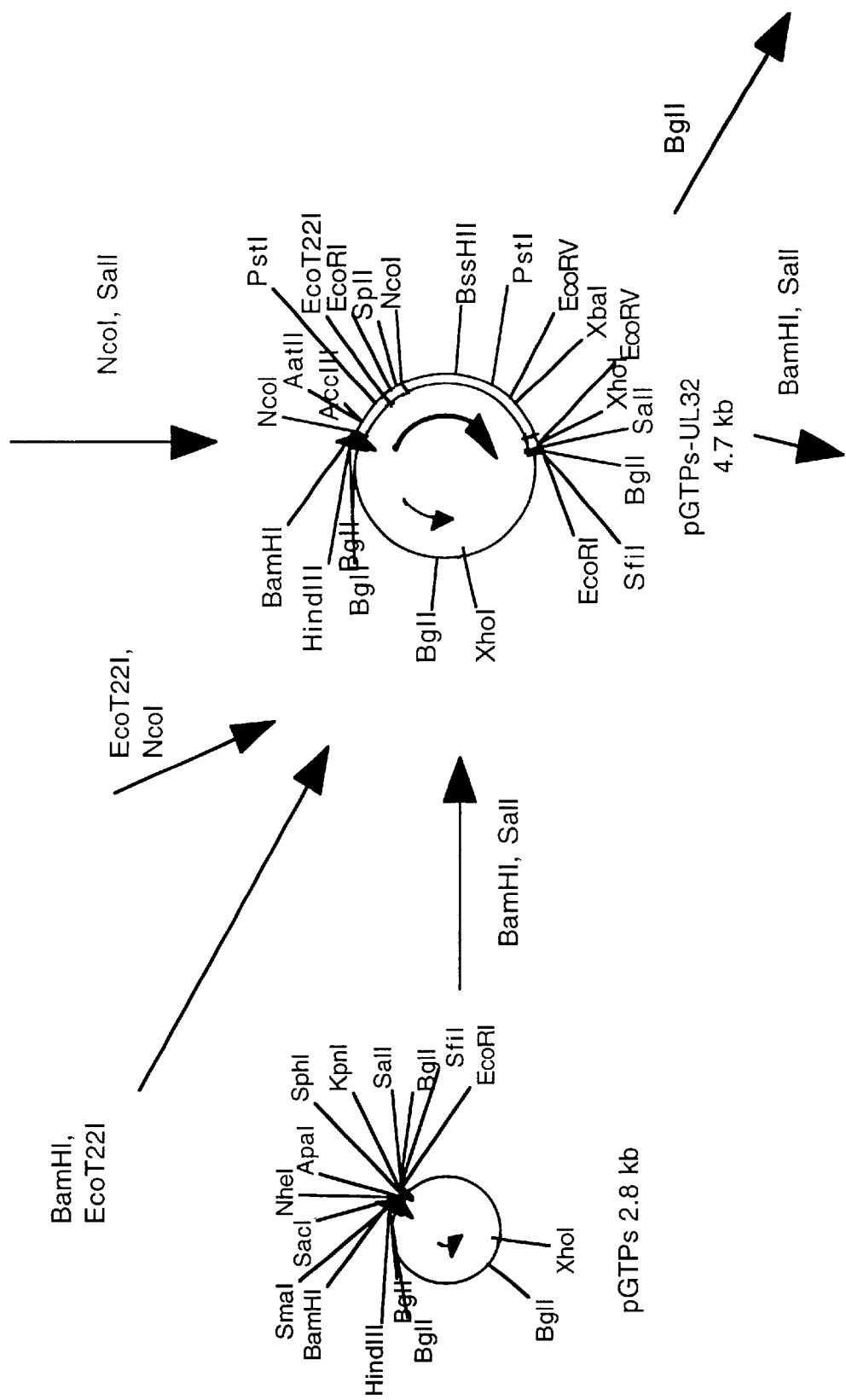
Figure 5C:
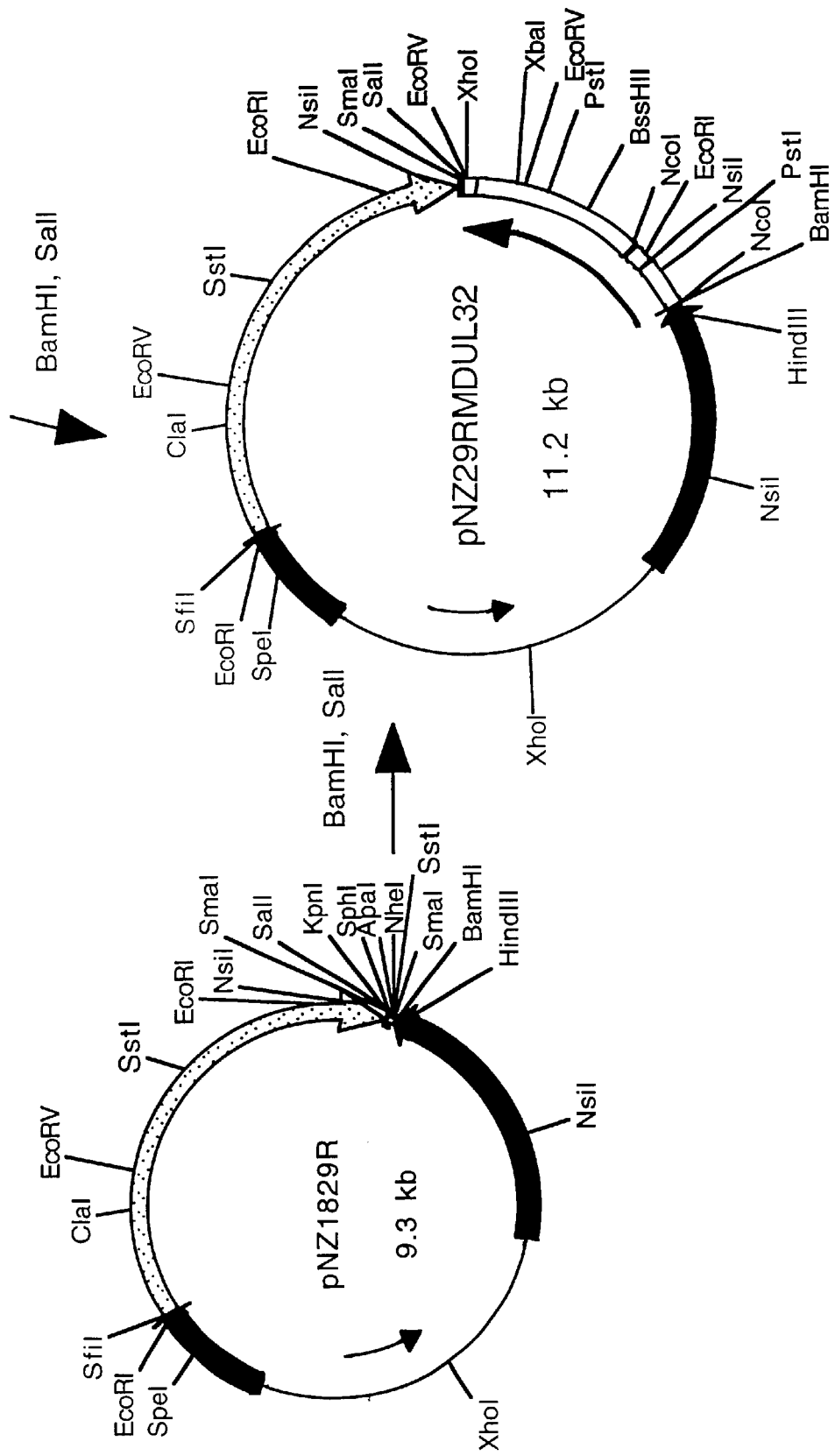
Figure 5D:
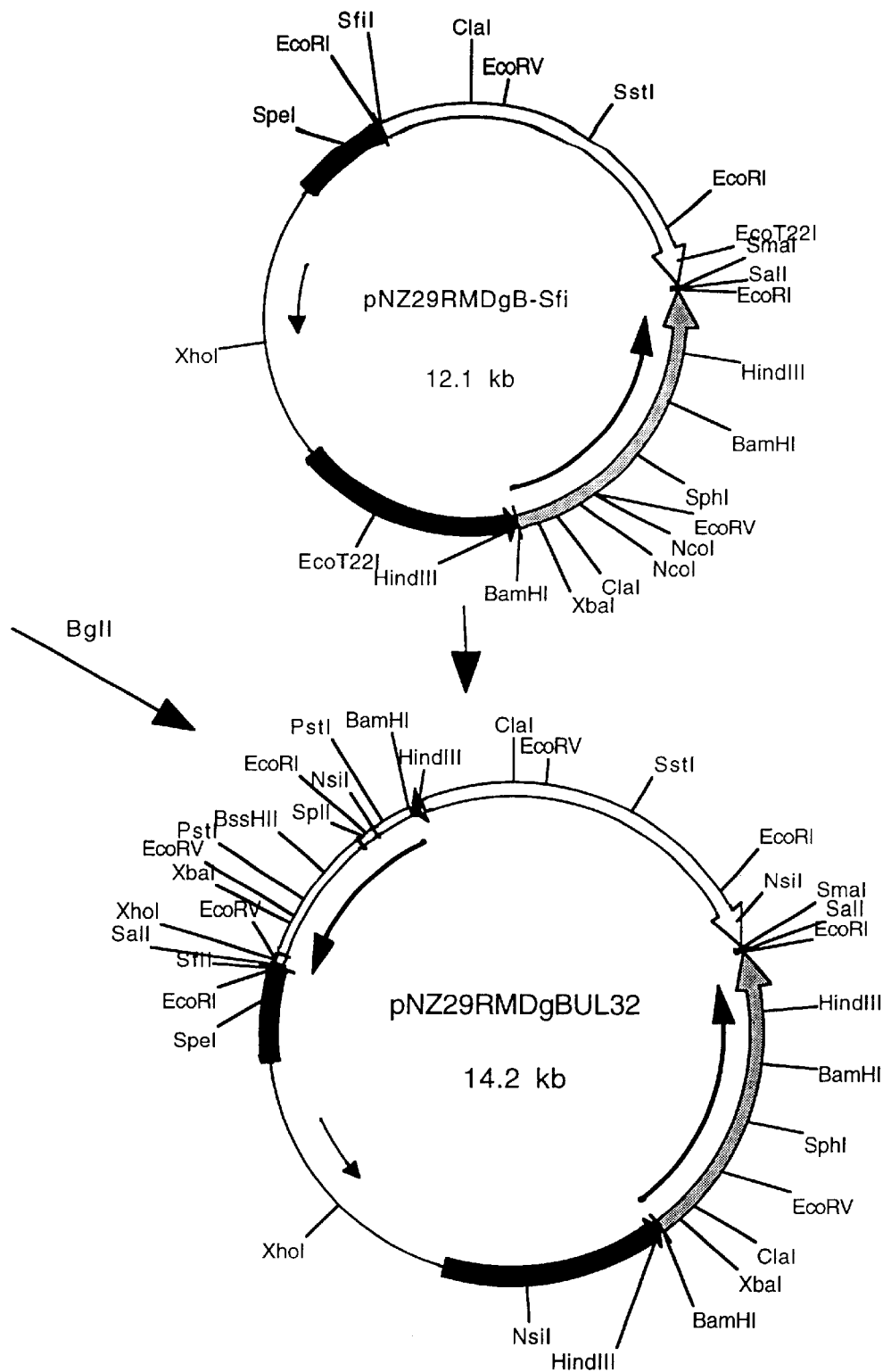
Figure 6:
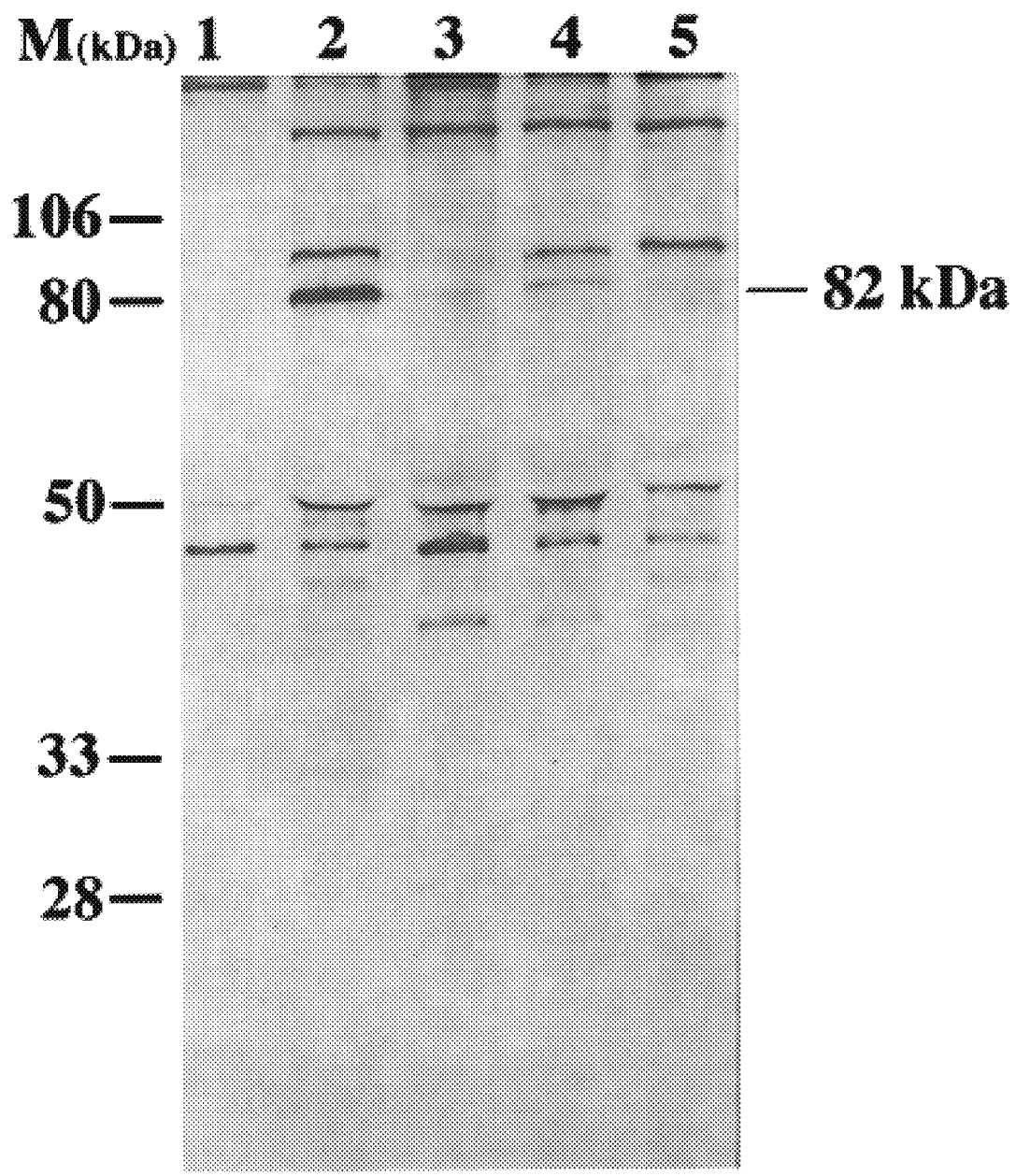
FIG. 6 shows immunoprecipitation using anti-trpE-UL32 fusion protein antibody. Lane 1: uninfected CEF cells; lane 2: CEF cells infected with MDV-1 (GA strain); lane 3: CEF cells infected with MDV-2 (SB-1 strain); lane 4: CEF cells infected with HVT (FC126 strain).
Figure 7:
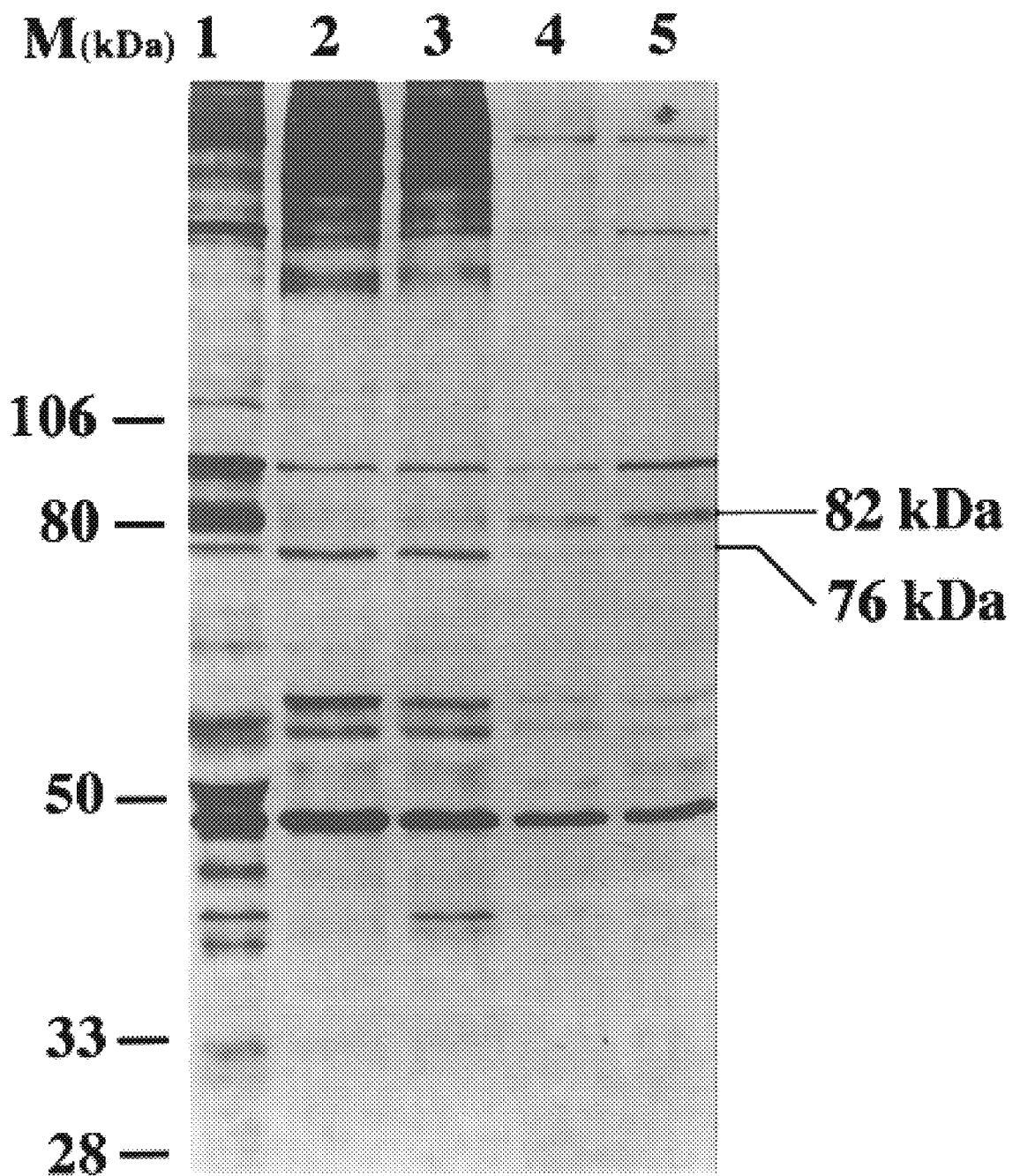
FIG. 7 shows the mobility shift assay of immunoprecipitants after treatment with endoglycosidases. Lane 1: no treatment; lanes 2 and 3: O-glycanase; lane 4: endo-H; lane 5: PNGase.

The plasmid pGTPs is constructed as follows. A synthetic DNA having the sequence 5'-AGCTGCCCCCCCGGCAAGCTTGCA-3' (SEQ ID NO:5) is inserted into the HindIII-PstI sites of pUC18. A synthetic DNA having the sequence 5'-TCGACATTTTTATGTAC-3' (SEQ ID NO:6) is then inserted into the SalI-KpnI sites, followed by insertion of the annealing product between the synthetic DNA having the sequence 5'-AATTCGGCCGGGGGGGCCAGCT-3'(SEQ ID NO:7) and a synthetic DNA having the sequence 5'-GGCCCCCCCGGCCG-3'(SEQ ID NO:8) into the SacI-EcoRI sites. Finally, the 140 bp HindIII-SalI fragment from pNZ1729R (U.S. Pat. No. 5,369,025) is inserted into the HindIII-SalI site of the resulting plasmid (FIG. 4).

EXAMPLE 4

Construction of Transfer Vectors pNZ29RMDUL32 and pNZ29RMDgBUL32

The polymerase chain reaction (PCR) was used to clone the MDV-UL32 gene and to remove the potential poxvirus early transcription termination signals (Yuen et al. *PNAS USA* 84:6417–6421 (1987)) from this gene. Three sets of primers were used:
Set 1:
  5'-CCCC<u>GGATCC</u>GGCCATGGCCAACCGC-3' (32-a) (SEQ ID NO:9) (BamHI site underlined) and 5'-AAGA <u>ATGCAT</u>AATCTGCCATCCAT-3' (32-bR) (SEQ ID NO:10) (EcoT22I site underlined);
Set 2:
  5'-GATT<u>ATGCAT</u>TCTTATGTTCCAAATG-3' (32-b) (SEQ ID NO:11) (EcoT22I site underlined) and 5'-ACAG <u>CCATGG</u>AGAAAGAAATGTCTCTGAATATC-3' (32-cR) (SEQ ID NO:12) (NcoI site underlined);
Set 3:
  5'-TTCT<u>CCATGG</u>CTGTTTTCGAACG-3'(32-c) (SEQ ID NO:13) (NcoI site underlined) and 5'-CCCC <u>GTCGAC</u>TTACACGTAGACTCCTAATG-3' (32-dR) (SEQ ID NO:14) (SalI site underlined).

MDV genomic DNA to be used as PCR templates was prepared as follows. CEF cells infected with the GA strain of MDV were recovered from tissue culture dishes by trypsinization, washed twice with PBS, and suspended in Proteinase K buffer (10 mM Tris-HCl, pH7.8, 5 mM EDTA, 0.5% SDS). Proteinase K (Boehringer Mannheim) was then added to a final concentration of 50 µg/ml, followed by incubation at 55° C. for 2 hours. Proteins were removed by two phenol/chloroform extractions. After addition of two volumes of ethanol followed by incubation at −20° C. for 20 minutes, genomic DNA of the GA strain of MDV was recovered by centrifugation.

Primer 32-a contains the nucleotide sequence of nucleotides 1–12 of SEQ ID NO:1, and has an upstream BamHI site for cloning. Primer 32-bR contains the nucleotide sequence of nucleotides 381–358 (reverse orientation, complementary strand) of SEQ ID NO:1 with mutations at nucleotide 376 (T to A) and nucleotide 379 (T to C) of the sense strand. Though by introduction of these mutations the nucleotide sequence of this region (371–385) changes from TATGCTTTTTTATGT (SEQ ID NO:15) to TATGCATTCT-TATGT (SEQ ID NO:16), there is no change in the amino acid sequence encoded by these sequences; they both code for Tyr-Ala-Phe-Leu-Cys (SEQ ID NO:17). The mutation at nucleotide 376 was introduced to create a cutting site for the restriction enzyme EcoT22I. The mutation at nucleotide 379 was introduced to remove the potential poxvirus early transcription termination signal (TTTTTNT; N being an arbitrary nucleotide).

Primer 32-b contains the nucleotide sequence of nucleotides 368–393 of SEQ ID NO:1, with mutations at nucleotide 376 (T to A) and nucleotide 379 (T to C) of the sense strand. Though by introduction of these mutations the nucleotide sequence of this region (371–385) changes from TATGCTTTTTTATGT (SEQ ID NO:18) to TATGCATTCT-TATGT (SEQ ID NO:16), there is no change in the amino acid sequence encoded by these sequences; they both code for Tyr-Ala-Phe-Leu-Cys (SEQ ID NO:17). The mutation at nucleotide 376 was introduced to create a cutting site for the restriction enzyme EcoT22I. The mutation at nucleotide 379 was introduced to remove the potential poxvirus early transcription termination signal (TTTTTNT; N being an arbitrary nucleotide).

Primer 32-cR contains the nucleotide sequence of nucleotides 529–561 (reverse orientation, complementary strand) of SEQ ID NO:1, with mutations at nucleotide 546 (T to C) and nucleotide 552 (G to C) of the sense strand. Though by introduction of these mutations the nucleotide sequence of this region (541–558) changes from CATTTTTTTCTG-CATGGC (SEQ ID NO.19) to CATTTCTTTCTCCATGGC (SEQ ID NO: 20), there is no change in the amino acid sequence encoded by these sequences; they both code for His-Phe-Phe-Leu-His-Gly (SEQ ID NO:22). The mutation at nucleotide 546 was introduced to remove the potential poxvirus early transcription termination signal (TTTTTNT;

N being an arbitrary nucleotide). The mutation at nucleotide 552 was introduced to created a cutting site for the restriction enzyme NcoI.

Primer 32-c contains the nucleotide sequence of nucleotides 548–570 of SEQ ID NO:1, with a mutation at nucleotide 552 (G to C) of the sense strand. Though by introduction of this mutation the nucleotide sequence of this region (541–558) changes from CATTTTTTTCTG-CATGGC (SEQ ID NO:19) to CATTTCTTTCTCCATGGC (SEQ ID NO:20), there is no change in the amino acid sequence encoded by these sequence; they both code for His-Phe-P he-Leu-His-Gly (SEQ ID NO:22). The mutation at nucleotide 552 was introduced to create a cutting site for the restriction enzyme NcoI.

Primer 32-dR contains the nucleotide sequence of nucleotides 1926–1907 (reverse orientation, complementary strand) of SEQ ID NO:1, and has an upstream SalI site for cloning.

Amplified fragments were cloned into the pGEM-T vector (Promega Corp., Madison, Wis.) and analyzed by DNA sequencing. Each of three plasmids, pGEM32ab, pGEM32bc, and pGEM32cd has an insert of the first, the second, and the third PCR fragment, respectively.

The 379 bp BamHI-EcoT22I fragment from pGEM32ab, the 180 bp EcoT22I-NcoI fragment from pGEM323bc, and the 1374 bp NcoI-SalI fragment from pGEM32cd were cloned into BamHI/SalI-digested pGTPs. The resulting plasmid was named pGTPsUL32. pNZ1829R was derived from pNZ1729R (Yanagida et al. *J. of Virology* 66:1402–1408 (1992)) and annealing oligos having the sequence 5'-GGCCCCCCCGGCCG-3' (SEQ ID NO:22) and 5'-AATTCGGCCGGGGGGGCCAGCT-3' (SEQ ID NO:23) between SacI and EcoRI sites located at the junction region of the lacZ gene and FPV DNA. A 1933 bp BamHI-SalI fragment from pGTPsUL32 was cloned into BamHI/SalI digested pNZ1829R to produce transfer vector pNZ29RMDUL32. Plasmid pNZ29RMDgBSfi was derived from pNZ29RMDgB-S (Yanagida et al. *J. of Virology* 66:1402–1408 (1992)) with annealing oligos having the sequences 5'-GGCCCCCCCGGCCG-3' (SEQ ID NO:22) and 5'-AATTCGGCCGGGGGGGCCAGCT-3' (SEQ ID NO:23) between SacI and EcoRI sites located at the junction region of the lacZ gene and FPV DNA. A 2066 bp BglII fragment from pGTPsUL32 was cloned into SfiI digested pNZ29RMDgBSfi to obtain transfer vector pNZ29RMDgBUL32.

EXAMPLE 5

Generation and Purification of Recombinant FPVs

Procedures for transfection of FPV-infected cells with the transfer vectors (pNZ29RMDUL32 or pNZ29RMDgBUL32 of Example 4) by electroporation and generation of recombinants have been described previously (Ogawa et al. *Vaccine* 8:486–490 (1990)). Approximately $3\times10^7$ CEF cells previously infected with FPV at a multiplicity of infection of 0.1 were transfected with 10 μg of transfer vector. After 3 days of incubation, progeny FPV were assayed for expression of lacZ in the presence of Bluo-gal (600 μg/ml) in the agar overlay. Blue plaques were removed from the agar and clone purified until all FPV plaques were blue.

The purified recombinant viruses were named recFPV/MD-UL32 or recFPV/MD-gB/UL32.

EXAMPLE 6

Expression of MDV gB and UL32 Antigens in Cell Culture

To test whether UL32 is translated in MDV-infected cells, CEF cells infected with GA strain, SB-1 strain, and HVT were radiolabeled, and immunoprecipitated with rabbit antiserum against the fusion protein trpE-UL32. The immunoprecipitated samples were analyzed by 8% SDS-PAGE followed by fluorography (FIG. 6). Anti-trpE-UL32 fusion protein antibody immunoprecipitated a protein with Mr 82,000 Da from the lysates of MDV-1 (GA strain) and HVT-infected cells, respectively (Lanes 2 and 4), but none from the lysates of MDV-2 (SB-1 strain) infected cells and CEF cells (Lane 3 and Lane 1). The apparent molecular weight is higher than that calculated according to the deduced amino acid sequence. To examine the type of carbohydrate modification in this glycoprotein, immunoprecipitated proteins were treated with endoglycosidases. After O-glycanase treatment, a mobility shift from Mr 82,000 to Mr 76,000 was observed (FIG. 7, Lanes 2 and 3). No mobility shift was observed when the immunoprecipitated protein was treated with endo-H and PNGase (FIG. 7, Lanes 4 and 5). Although there are two potential N-linked glycosylation sites in the amino acid sequence of UL32, they are not likely used. The size of the protein after O-glycanase treatment is closer to that calculated from the deduced amino acid sequence.

In order to show that recFPV/MD-gB/UL32 synthesizes both the gB antigen and the UL32 antigen, CEF cultures infected with this virus were examined by IF using antibodies specifically raised against these antigens. CEF cultures infected with recFPV/MD-gB/UL32 were incubated at 37° C. until typical FPV plaques developed. These cultures were fixed in cold acetone, and then reacted with appropriate dilutions of monoclonal antibody specific to MDV gB antigen (Silva et al. *Virology* 136:307–320 (1984)) or a monoclonal antibody specific to MDV UL32 antigen. These cultures were then reacted with fluorescein-conjugated anti-mouse immunoglobulins, and after thorough washing to remove non-specific staining, they were examined microscopically under ultraviolet (UV) illumination. CEF cultures infected with non-recombinant parental FPV were similarly stained. Specific cytoplasmic and membrane staining of cells was observed in cultures infected with the recFPV/MD-gB/UL32 with each of the monoclonal antibodies and not in cultures infected with the non-recombinant parental FPV. These observations clearly show that the recombinant virus is capable of synthesizing the products of the gB and UL32 genes of MDV in cell cultures.

Primary CEF cultures infected with either parental or recombinant FPV at an moi of 5 were incubated at 37° C. for 4 hours. Then, the medium was replaced with 1 ml of fresh methionine-free medium and incubated for another hour. About 40 μCi of $^{35}$S-methionine (NEN, Wilmington, Del.) were then added, and the cultures were incubated for an additional 5 hours. Cells were washed twice in PBS, scraped, and transferred to a 15 ml Falcon tube. Cells were centrifuged, resuspended in lysis buffer (150 mM NaCl, 1% sodium deoxycholate, 1% Triton X-100, 0.1% SDS, and 10 mM Tris HCl, pH 7.5) and incubated at room temperature for 30 minutes. One half volume of 10% (v/v) *S. aureus* Cowan 1 (SAC) was added to the cell lysate, and incubated for 30 minutes on ice. The lysate was then centrifuged, and the supernatant was collected. About 3 μl of monoclonal antibody 1AN86 against MD gB (Silva et al. *Virology* 136:307–320 (1984)) were added to 100 μl of lysate and incubated for 30 minutes on ice. An equal volume of 10% (v/v) SAC was added and incubated on ice for 30 minutes. Immunoprecipitates were then washed, suspended in sample buffer, and then boiled. After centrifugation, the supernatant was analyzed by sodium dodecylsulphate-polyacrylamide gel electrophoresis (Laemmli *Nature* 207:680–685 (1970).

Figure 8:
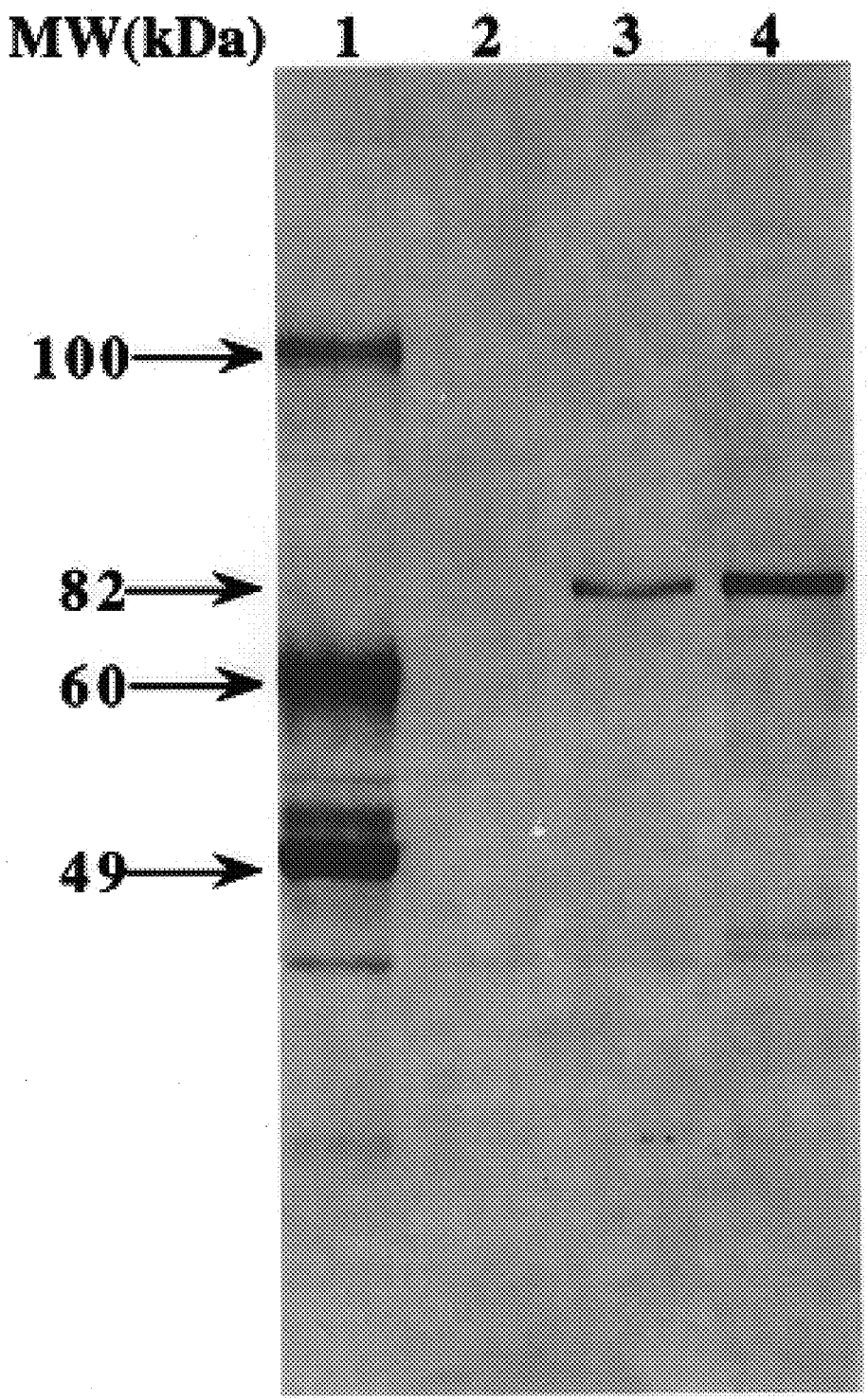
FIG. 8 shows the immunoprecipitation of cells infected with recFPV/MD-gB/UL32 or with the GA strain of MDV.

FIG. 8 shows the results of immunoprecipitation with monoclonal antibodies specific for MD gB and gp82 proteins. Lane 1: CEF cells infected with recFPV/MD-gB/UL32 with monoclonal antibody for gB; Lane 2: CEF cells infected with wild-type FPV with monoclonal antibody for gB; Lane 3: CEF cells infected with recFPV/MD-gB/UL32 with monoclonal antibody for gp82; Lane 4: CEF cells infected with the GA strain of MDV with monoclonal antibody for gp82. Three identical bands of 100 kd, 60 kd, and 49 kd in molecular weight were observed in extracts of cells infected with recFPV/MD-gB/UL32 (FIG. 8, lane 1). A single band of 82 kd was observed using Mab against gp82 in the extract of double recombinants. These results demonstrate that recFPV/MD-gB/UL32 expresses both gB antigen complex and UL 32 antigen.

EXAMPLE 7

Protection of Antibody-Negative Chickens With Recombinant FPVs Expressing the gB or UL32 Gene, or Both, Against a Very Virulent Strain of MDV (Md5)

Separate groups of 1-day-old chickens from 15×7 AB(−) chicken line susceptible to MD were vaccinated with $10^5$ plaque forming units (PFU) of recFPV/MD-gB (U.S. Pat. No. 5,369,025; Example 4), $10^5$ PFU of recFPV/MD-UL32 (Example 5), $10^5$ PFU of recFPV/MD-gB/UL32 (Example 5), or $2\times10^3$ PFU of the FC126 strain of HVT. Another group of similar chickens was kept unvaccinated. All were kept in strict isolation. At 6 days of age, all chickens were challenged with $5\times10^2$ PFU of the very virulent Md5 strain of MDV (Witter et al. *Avian Dis.* 24:210–232 (1980)). A fifth group of chickens was neither vaccinated nor challenged. Mortality caused by MD was recorded during the trial, and at the end of the 8 week trial, all chickens were examined for gross lesions and tumors typical of MD. The results of this study are presented in Table 1.

TABLE 1

Vaccination trial and evaluation of synergistic effects of recombinant FPV expressing the gB and UL32 genes of MDV in comparison with a conventional vaccine (FC126 of HVT) in Ab(−) chickens challenged with the Md5 isolate of MDV at 5 days post vaccination

| Vaccine | No. tested | MD Death | MD lesion | % protection |
| --- | --- | --- | --- | --- |
| recFPV/MD-gB | 14 | 0 | 4 | 71 |
| recFPV/MD-gB/UL32 | 14 | 0 | 0 | 100 |
| recFPV/MD-UL32 | 14 | 2 | 12 | 14 |
| HVT | 14 | 0 | 3 | 79 |
| none | 14 | 11 | 14 | 0 |
| none-no challenge | 14 | 0 | 0 | |

A significant number of unvaccinated chickens died of MD before the end of the trial. On the other hand, chickens vaccinated with recFPV/MD-gB, recFPV/MD-gB/UL32, or HVT were fully protected from death due to MD. The majority of chickens vaccinated with recFPV/MD-UL32 were protected from death due to MD, although they were not significantly protected from MD lesions. Seventy-one percent of chickens vaccinated with recFPV/MD-gB were similarly protected from MD lesions as compared to 79% of those vaccinated with HVT. Those vaccinated with recFPV/MD-gB/UL32 were fully protected (100%) against the very virulent Md5 strain of MDV, and showed no mortality and no lesions typical of MD. recFPV/MD-UL32 confers only 14% protection, but the death count is low, i.e., only 2 chickens. The protective effect of recFPV/MD-gB/UL32 is not merely the sum of the effects of recFPV/MD-gB+ recFPV/MD-UL32. Rather, the UL32 gene unexpectedly enhances the effect of the gB antigen gene.

EXAMPLE 8

Protection of Antibody-Positive Chickens With Recombinant FPVs Expressing the gB or the UL32 Gene, or Both, Against a Very Virulent Strain of MDV (Md5)

Two sets of experiments were performed. Each set was performed as follows. Separate groups of 1-day-old chickens from 15×7 Ab (+) chicken line susceptible to MD were vaccinated with $10^5$ plaque forming units (PFU) of recFPV/MD-gB, $10^5$ PFU of recFPV/MD-UL32, $10^5$ PFU of recFPV/MD-gB/UL32, $2\times10^3$ PFU of HVT, $2\times10^3$ PFU of CVI988/Rispens (Rispens), $10^3$ PFU of SB-1+$10^3$ PFU of HVT, $10^5$ PFU of recFPV/MD-gB+$2\times10^3$ PFU of HVT or $10^5$ PFU of recFPV/MD-gB/UL32+$2\times10^3$ PFU of HVT vaccines. Another group of similar chickens was kept unvaccinated. All were kept in strict isolation. At 6 days of age all were challenged with $5\times10^2$ PFU of the very virulent Md5 strain of MDV. A tenth group of chickens were neither vaccinated nor challenged. Mortality caused by MD was recorded during the trial and at the end of the 8 week trial all chickens were examined for gross lesions and tumors typical of MD. The results of this study are presented in Table 2.

TABLE 2

Vaccination trial and evaluation of synergistic effects of recombinant FPV expressing the gB and UL32 genes of MDV in comparison with monovalent and bivalent conventional vaccines in Ab(+) chickens challenged with the Md5 isolate of MDV at 5 days post vaccination

| | Trial 1 | | | | Trial 2 | | | | Summary | | | |
| --- | --- | --- | --- | --- | --- | --- | --- | --- | --- | --- | --- | --- |
| vaccine | MD | test | % MD | PI | MD | test | % MD | PI | MD | test | % MD | PI |
| recFPV/MD-gB | 11 | 15 | 73 | 17 | 8 | 16 | 50 | 47 | 19 | 31 | 61 | 33 |
| recFPV/MD-UL32 | 10 | 14 | 71 | 19 | 13 | 17 | 76 | 19 | 23 | 31 | 74 | 18 |

TABLE 2-continued

Vaccination trial and evaluation of synergistic effects of recombinant FPV expressing the gB and UL32 genes of MDV in comparison with monovalent and bivalent conventional vaccines in Ab(+) chickens challenged with the Md5 isolate of MDV at 5 days post vaccination

|  | Trial 1 | | | | Trial 2 | | | | Summary | | | |
| --- | --- | --- | --- | --- | --- | --- | --- | --- | --- | --- | --- | --- |
| vaccine | MD | test | % MD | PI | MD | test | % MD | PI | MD | test | % MD | PI |
| recFPV/MD-gB/UL32 | 3 | 17 | 18 | 80 | 5 | 17 | 29 | 69 | 8 | 34 | 24 | 74 |
| HVT | 5 | 15 | 33 | 62 | 11 | 17 | 65 | 31 | 16 | 32 | 50 | 45 |
| Rispens | 6 | 17 | 35 | 60 | 8 | 16 | 50 | 47 | 14 | 33 | 42 | 53 |
| SB1 + HVT | 8 | 17 | 47 | 47 | 2 | 16 | 13 | 87 | 10 | 33 | 30 | 67 |
| gB + HVT | 4 | 17 | 24 | 73 | 3 | 17 | 18 | 81 | 7 | 34 | 21 | 77 |
| gB/UL32 + HVT | 2 | 15 | 13 | 85 | 3 | 17 | 18 | 81 | 5 | 32 | 16 | 83 |
| None | 14 | 16 | 88 | | 16 | 17 | 94 | | 30 | 33 | 91 | |
| None (no chal.) | 0 | 17 | 0 | | 0 | 17 | 0 | | 0 | 34 | 0 | |

Moderate levels of protection were observed in chickens vaccinated with recFPV/MD-gB, recFPV/MD-UL32 (U.S. Pat. No. 5,369,025 example 4) (example 5) or HVT (cell associated FC126 strain of HVT). Whereas chickens vaccinated with recFPV/MD-gB/UL32 were significantly well protected (74% on average protection index (PI={% MD in control−(% MD in test)/(%MD in control)}×100, which was even better than widely used commercial bivalent SB-1 (another Serotype 2 vaccine (Witter et al., Avian Dis., 31 829–844 (1987))+HVT (67%) or CVI988/Rispens (53%), which is considered to be the best monovalent MDV vaccine in commercial use in Europe.

Although either recFPV/MD-gB or HVT alone induced protection of 33% and 45%, respectively, a combination of these two vaccines showed a significant synergism of protection (77%).

EXAMPLE 9

Protection and Synergism by Recombinant Fowlpox Vaccines Expressing Genes from Marek's Disease Virus

Overview

Recombinant fowlpox viruses (recFPV) were constructed to express genes from serotype 1 Marek's disease virus (MDV) coding for glycoproteins B, C, D, and gp82 (gB, gC, gD, and UL32) and tegument proteins UL47 and UL48, as well as genes from serotype 2 and 3 MDV coding for glycoprotein B (gB2 and gB3). These recFPVs, alone and in various combinations, including combinations of recFPV/MD-gBs with turkey herpesvirus (HVT), were evaluated for ability to protect maternal antibody positive (ab+) and negative (ab−) chickens against challenge with highly virulent MDV isolates. The protective efficacy was also compared to that of prototype MD vaccines. No protection was induced in ab+ chickens by recFPV expressing gC, gD, UL47, or UL48. In contrast, the recFPV/MD-gB construct protected about 23% of ab+ chickens against MDV challenge compared to 26% for cell-associated HVT. Levels of protection by recFPV/MD-gBs of different MDV serotypes was highest for gB, intermediate for gB2, and lowest for gB3. When recFPV/MD-gB was combined with cell-associated HVT, protection was enhanced by an average of 138% compared to the best component monovalent vaccine, and the mean level of protection was 59% compared to 67% for the HVT+SB-1 bivalent vaccine. Relatively high protection (50%) and enhancement (200%) was also observed between recFPV/MD-gB and cell-free HVT. These results suggest a specific synergistic interaction between recFPV/MD-gB and HVT, possibly analogous to that previously described between serotype 2 and 3 viruses. Levels of protection by recFPV/MD-gB alone or by bivalent recFPV/MD-gB+cell-associated HVT were similar to those of conventional cell-associated MD vaccines. However, the bivalent recFPV/MD-gB+cell-free HVT vaccine was clearly more protective than cell-free HVT alone and, thus, may be the most protective, entirely cell-free MD vaccine thus far described.

Three serotypes of MDV have been described (2,6): serotype 1 includes pathogenic isolates of chicken origin and their attenuated derivatives, serotype 2 includes the naturally apathogenic isolates of chicken origin, and serotype 3 includes the naturally apathogenic isolates of turkey origin known as turkey herpesvirus (HVT) (25). Vaccines derived from all three serotypes offer different levels of protection against the disease either alone or in bivalent and trivalent combinations (24).

Glycoprotein B (gB) is highly conserved among herpesviruses. In herpes simplex virus, it has been shown to be essential for virus infectivity and thus involved in virus penetration in host cells (4,5). Antibodies to this glycoprotein are known to neutralize the virus (4,5). Recently, gBs from all three serotypes of MDV were shown to be also highly conserved (31) with predicted amino acid identities of 83 and 82% for gB2 and gB3 when compared with gB (12). Analysis of the gB complex of MDV with a neutralizing monoclonal antibody showed that it is composed of a precursor 100 kda molecular weight protein and two cleavage products of 60 kda and 49 kda glycoproteins (30). This monoclonal antibody recognized only the gB of serotype 1 and 3 and not that of serotype 2 (15).

Preliminary trials indicated that recFPV/MD-gB induced high levels of protection against MD challenge in maternal antibody negative chickens (9). Under the test conditions employed, the magnitude of the protection induced by recFPV/MD-gB approached 100% but could not be differentiated from that induced by HVT.

We describe below the use of recFPVs expressing gB, other glycoproteins, and tegument proteins of serotype 1 MDV as well as those expressing gB from serotypes 2 and 3 of MDV, either alone or in combination with HVT, to protect against MD in chickens with MDV maternal antibodies.

Viruses

Prototype vaccine viruses included the R2/23 (20) and CVI988/Rispens (10, 21) strains of serotype 1, the SB-1 (13)

and 301B/1 (17, 18) strains of serotype 2, and the FC126/2 (19) strain of HVT (serotype 3). Both cell-associated and cell-free stocks of HVT were used. The cell-free HVT consisted of two different vaccine preparations of the FC126 strain (Solvay Animal Health, Mendota Heights, Minn.). All other vaccine stocks were prepared in the inventors' laboratory. The very virulent Md5 (26) and RB1B (14) strains of MDV were used as challenge viruses. A large-plaque-forming clone (8) from a cell-culture-propagated vaccine isolate of fowlpox virus (FPV) was used as the parent virus to construct recombinant FPVs expressing MDV genes.

Construction of Recombinant FPV

Cloning of MDV genes and construction of recFPVs were essentially as reported earlier (28). Recombinants were constructed that expressed genes from serotype 1 Marek's disease virus (MDV) coding for glycoproteins B (gB) (12), C (gC) (3), D (gD) (11), gp82 (UL32), and tegument proteins UL47 and UL48 (29), as well as genes from serotype 2 and 3 MDV coding for glycoprotein B (gB2 and gB3) (31). The sequence TTTTTNT that has been reported to terminate early transcription in poxvirus replication was modified in MDV genes whenever present by site specific mutagenesis (28). MDV genes were inserted into a multiple cloning site constructed within a nonessential region of FPV DNA downstream from a strong synthetic pox virus promoter into pNZ1729R insertion vector (28). This vector contained the lacZ bacterial gene which expresses the beta galactosidase of *E. coli*. The lacZ gene was downstream from a weak FPV promoter and in the opposite direction from the MDV gene.

Chicken embryo fibroblast (CEF) cultures infected for 5 hours at a multiplicity of infection of 5 with a vaccine isolate of FPV were transfected with 10 μg of transfer vector containing different genes of MDV. Using the expression of lacZ as an indicator, cloned recombinant viruses were identified and purified through several CEF passages. Pure recombinant virus was obtained after 4 serial passages of each clone. Two blind passages were made to ascertain the purity of each recombinant. Stocks of purified recFPV were stored at −70° C., titered on CEF by plaque assay, and used for vaccination of chickens.

Chickens

Chickens were $F_1$ progeny of line $15I_5$, males and $7_1$ females. For most experiments, these were from breeder hens vaccinated with all three MD viral serotypes as described (18) and were considered positive for maternal antibodies (ab+). In one trial, chickens of the same $F_1$ cross were from unvaccinated breeder hens that were free of antibodies to MDV and HVT; these were considered negative for maternal antibodies (ab−). All breeder chickens were maintained at the Avian Disease and Oncology Laboratory and were free of antibodies to avian leukosis virus, reticuloendotheliosis virus and various other poultry pathogens.

Protection Trials

Groups of 12 to 17 chickens were vaccinated at 1 day of age with $10^6$ plaque forming units (PFU) of recFPV vaccines by the wingweb (WW) route in trial 1 or by the intraabdominal (IA) route in all other trials. Monovalent and polyvalent MDV and HVT vaccines were administered to chickens by the IA route at a dose of 2000 PFU except where otherwise indicated. The cell-free HVT used in trials 2 and 3 were from two different batches. For polyvalent recFPV+MDV vaccines, each component was administered by a separate inoculation. For polyvalent vaccines composed of two MDV strains, the viruses were mixed and given as a single inoculation. Ab+ chickens were used in trials 1–4; ab− chickens were used in trial 5. Following vaccination, chickens were housed in modified Horsfall-Bauer isolators.

At the 6th day post hatch, groups of vaccinated and unvaccinated chickens were challenged by IA inoculation of 500 PFU of strain Md5 (trials 1–4) or strain RB1B (trial 5). Mortality during the course of the experiment was recorded and chickens were examined for gross MD lesions. At about 56 days postchallenge (range 48–62), the remaining chickens were killed and examined for gross MD lesions.

The percent MD based on the number of chickens that died or were killed and had gross MD lesions divided by the number of chickens at risk (total less birds dying of other causes)×100 was determined for each group. The percent protection was calculated for each vaccinated group as the percent MD in unvaccinated, challenged controls less the percent MD in the vaccinated, challenged group divided by the percent MD in the unvaccinated, challenged controls×100. The percent synergism was calculated for each bivalent-vaccinated group as the percent protection of the bivalent vaccine minus the percent protection of the better of the two constituent monovalent vaccines divided by the percent protection of the best monovalent vaccine×100. Five trials were conducted; each trial consisted of 2 or 3 replicates. Statistical analysis was performed on pooled data from all replicates. Differences in percent protection were analyzed by computing interaction chi-square values (16). The significance of percent synergism values was analyzed by comparing interaction chi-square values of the bivalent vaccine with that of the best monovalent vaccine (22). Differences were considered to be significant when $P<0.05$.

Comparative Efficacy of recFPV Expressing Different MDV Genes (Trial 1)

Chickens were immunized with five recFPVs with inserted serotype 1 MDV genes encoding three different glycoproteins (gB, gC and gD) and two tegument proteins (UL47 and UL48). Mixtures of gB+gC and gB+gC+gD+UL47+UL48 were also tested. Other results, including those obtained with UL32, are shown in Tables 1 and 2. Conventional MD vaccines were included as controls. Results (Table 3) indicate that recFPV/MD-gB was the only recombinant among the five tested that provided significant protection. The use of other FPV recombinants expressing gC, gD, UL47 or UL48 genes in combination with the recFPV/MD-gB did not increase the percent protection.

TABLE 3

Vaccination trials to evaluate FPV recombinants expressing different glycoproteins and tegument proteins of serotype 1 MDV (Trial 1)

| | Replicate 1 | | | Replicate 2 | | | Replicate 3 | | | Summary | | |
|---|---|---|---|---|---|---|---|---|---|---|---|---|
| Vaccine[A] | N | % MD | % Protection | N | % MD | % Protection | N | % MD | % Protection | N | % MD | % Protection[B] |
| recFPV monovalent: | | | | | | | | | | | | |
| recFPV/MD-gB | 15 | 73 | 27 | 17 | 88 | 12 | 17 | 82 | 18 | 49 | 82 | 18 cd |
| FPV/gC | 16 | 100 | 0 | 17 | 100 | 0 | 17 | 100 | 0 | 50 | 100 | 0 a |
| FPV/gD | 17 | 100 | 0 | 17 | 100 | 0 | 17 | 100 | 0 | 51 | 100 | 0 a |
| FPV/UL47 | 14 | 93 | 7 | 16 | 100 | 0 | 17 | 100 | 0 | 47 | 98 | 2 ab |
| FPV/UL48 | 14 | 93 | 7 | 15 | 100 | 0 | 15 | 93 | 7 | 44 | 96 | 5 abc |
| recFPV polyvalent: | | | | | | | | | | | | |
| recFPV/MD-gB + gC | 15 | 67 | 33 | 17 | 82 | 18 | 16 | 100 | 0 | 48 | 83 | 17 cd |
| recFPV/MD-gB + gC + gD + UL47 + UL48 | 17 | 94 | 6 | 17 | 71 | 29 | 17 | 94 | 6 | 51 | 86 | 13 bcd |
| Controls: | | | | | | | | | | | | |
| HVT (CA) | 17 | 41 | 59 | 17 | 88 | 12 | 17 | 100 | 0 | 51 | 77 | 24 d |
| HVT (CA) + 301B/1 | 17 | 18 | 82 | 17 | 65 | 35 | 17 | 29 | 71 | 51 | 32 | 63 e |
| R2/23 | 17 | 24 | 76 | 17 | 41 | 59 | 11 | 27 | 73 | 45 | 52 | 69 e |
| None | 16 | 100 | | 17 | 100 | | 17 | 100 | | 50 | 97 | |

[A]CA = cell-associated.
[B]Values followed by the same lower-case letter do not differ ($P < 0.05$).

Protective Synergism Between recFPV/MD-gB and HVT (Trials 2 and 3)

In trial 2, bivalent vaccines composed of recFPV/MD-gB with cell-associated HVT, cell-free HVT or CVI988/Rispens were evaluated for synergism by comparison of the percent protection with that of appropriate monovalent vaccines. Pooled data from three replicates (Table 4) show that percent protection was 8% for recFPV/MD-gB and 18% for cell-associated HVT but, when both were combined as a bivalent vaccine, protection was 66%, a 267% increase compared to cell-associated HVT alone. Enhancement in individual replicates varied from 183 to 477%. Similarly, the recFPV/MD-gB combined with cell-free HVT protected 45% of chickens compared to 8% for each of the individual components, a 462% increase (range 218 to >500). No synergism was apparent, however, when recFPV/MD-gB was combined with CVI988/Rispens.

Trial 3 included groups immunized with recFPV/MD-gB or recFPV/gB3, both alone and in combination with cell-associated HVT. The results, presented in Table 5, resembled those of trial 2. Protection by the recFPV/MD-gB+HVT vaccine (48%) was enhanced by 140% (range 72–173% in 3 replicates) compared to HVT alone (20%). The recFPV/gB3 construct failed to provide any significant protection or synergism.

TABLE 4

Vaccination trials to evaluate synergism between the FPV/gB1 recombinant and MDV vaccines of serotypes 1 and 3 (Trial 2).

| | Replicate 1 | | | Replicate 2 | | | Replicate 3 | | | Summary | | | |
|---|---|---|---|---|---|---|---|---|---|---|---|---|---|
| Vaccine[A] | N | % MD | % Protection | N | % MD | % Protection | N | % MD | % Protection | N | % MD | % Protection[B] | % Synergism[C] |
| recFPV Monovalent: | | | | | | | | | | | | | |
| recFPV/MD-gB | 17 | 88 | 12 | 17 | 100 | 0 | 17 | 88 | 12 | 51 | 92 | 8 a | |
| recFPV Polyvalent: | | | | | | | | | | | | | |
| recFPV/MD-gB + FC126 (CA) | 17 | 49 | 51 | 16 | 25 | 75 | 17 | 35 | 65 | 50 | 43 | 66 cd | 267 * |
| recFPV/MD-gB + FC126 (CF) | 16 | 50 | 51 | 16 | 75 | 25 | 17 | 41 | 59 | 49 | 55 | 45 b | 462 * |
| recFPV/MD-gB + CVI988/Rispens | 17 | 11 | 88 | 17 | 11 | 88 | 17 | 43 | 56 | 50 | 22 | 78 cde | <1 ns |
| Controls: | | | | | | | | | | | | | |
| HVT (CA) | 17 | 82 | 18 | 16 | 87 | 13 | 17 | 76 | 24 | 50 | 82 | 18 b | |
| HVT (CF) | 17 | 88 | 16 | 16 | 100 | 0 | 17 | 88 | 12 | 50 | 92 | 8 a | |
| HVT (CA) + SB-1 | 16 | 6 | 94 | 17 | 18 | 22 | 17 | 29 | 71 | 50 | 18 | 82 de | |
| HVT (CF) + SB-1 | 17 | 17 | 83 | 16 | 43 | 56 | 17 | 47 | 53 | 50 | 36 | 64 bcd | |
| HVT (CA) + 301B/1 | 17 | 11 | 88 | 13 | 23 | 77 | 17 | 0 | 100 | 47 | 11 | 89 e | |
| CVI988/Rispens | 16 | 6 | 94 | 17 | 12 | 88 | 17 | 53 | 88 | 47 | 38 | 90 e | |

TABLE 4-continued

Vaccination trials to evaluate synergism between the FPV/gB1 recombinant and MDV vaccines of serotypes 1 and 3 (Trial 2).

| Vaccine[A] | Replicate 1 | | | Replicate 2 | | | Replicate 3 | | | Summary | | | |
|---|---|---|---|---|---|---|---|---|---|---|---|---|---|
| | N | % MD | % Protection | N | % MD | % Protection | N | % MD | % Protection | N | % MD | % Protection[B] | % Synergism[C] |
| R2/23 | 13 | 0 | 100 | 17 | 12 | 53 | 17 | 12 | 47 | 50 | 10 | 62 bc | |
| None | 17 | 100 | — | 17 | 100 | — | 17 | 100 | — | 51 | 100 | — | |

[A]CA = cell-associated; CF = cell-free.
[B]Values followed by the same lower-case letter do not differ (P < 0.05).
[C]Synergism based on a comparison of protection with that of the best constituent monovalen vaccine (* = P < 0.05; ns = P > 0.05).

TABLE 5

Vaccination trials to evaluate synergism between different FPV/gB recombinants and HVT, and the comparative efficacy of different FPV/gB recombinants (Trial 3).

| Vaccine[A] | Replicate 1 | | | Replicate 2 | | | Replicate 3 | | | Summary | | | |
|---|---|---|---|---|---|---|---|---|---|---|---|---|---|
| | N | % MD | % Protection | N | % MD | % Protection | N | % MD | % Protection | N | % MD | % Protection[B] | % Synergism[C] |
| recFPV Monovalent: | | | | | | | | | | | | | |
| recFPV/MD-gB | 15 | 73 | 27 | 17 | 82 | 18 | 17 | 88 | 12 | 49 | 82 | 18 b | |
| recFPV/MD-gB2 | 17 | 53 | 47 | 17 | 47 | 53 | 17 | 94 | 6 | 51 | 65 | 35 bc | |
| recFPV/MD-gB3 | 15 | 100 | 0 | 16 | 100 | 0 | 17 | 94 | 6 | 48 | 98 | 2 a | |
| recFPV Polyvalent: | | | | | | | | | | | | | |
| recFPV/MD-gB + HVT (CA) | 15 | 47 | 53 | 14 | 50 | 50 | 17 | 59 | 41 | 46 | 52 | 48 cd | 140 * |
| recFPV/MD-gB3 + HVT (CA) | 14 | 64 | 36 | 17 | 88 | 12 | 17 | 59 | 41 | 48 | 71 | 29 bc | 45 ns |
| Controls: | | | | | | | | | | | | | |
| HVT (CA) | 5 | 80 | 20 | 17 | 71 | 29 | 34 | 85 | 15 | 56 | 80 | 20 b | |
| HVT (CA) + SB-1 | 17 | 29 | 71 | 17 | 35 | 65 | 17 | 53 | 47 | 51 | 39 | 61 de | |
| CVI988/Rispens | 17 | 41 | 59 | 17 | 24 | 76 | 17 | 41 | 59 | 51 | 35 | 65 de | |
| None | 14 | 100 | | 17 | 100 | | 17 | 100 | | 48 | 100 | | |

[A]CA = cell-associated.
[B]Values followed by the same lower-case letter do not differ (P < 0.05).
[C]Synergism based on a comparison of protection with that of the best constituent monovalen vaccine (* = P < 0.05; ns = P > 0.05).

Efficacy of Conventional Vaccines

Conventional cell-associated vaccines were used as controls in trials 1–3. Protection was least with cell-free HVT, intermediate with cell-associated HVT, and greatest with bivalent serotype 2+3 or serotype 1 vaccines. The relative efficacy of these vaccines was consistent with previous observations.

Dosage and Administration of the Vaccine

The vaccine described above can be administered in a variety of different ways:

1. By inoculation of recFPV/gB at a dose of $10^2$ to $10^6$ PFU per chick, more preferably at a dose of $10^4$ to $10^6$ PFU per chick, given by either the intraabdominal, wingweb, intramuscular, or subcutaneous route plus separate inoculation of cell-associated HVT vaccine at a dose of 500 to 20,000 PFU, more preferably at a dose of 2,000 to 10,000 PFU, by the intraabdominal, intramuscular, or subcutaneous route;
2. As in 1, above, except that cell-free HVT vaccine is substituted for cell-associated HVT vaccine;
3. As in 1, above, except that the recFPV/gB and HVT are combined in the same inoculum;
4. As in 1, above, except that the recFPV/gB may be replaced by recFPV vaccines expressing gB plus other inserted genes from MDV or other sources; or
5. As in 1, above, when the HVT is derived from any of the recognized strains, including FC126, that can be classified as a serotype 3 Marek's disease virus.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

References Cited In Example 9

1. Brunovskis et al. In: 4th International Symposium on Marek's Disease, 19th World's Poultry Congress, Vol. 1, World's Poultry Science Assn., Amsterdam, pp. 118–122 (1992).
2. Bulow et al. Avian Pathology, 4:133–146 (1975).
3. Coussens et al. J. Virol. 62:467–476 (1988).
4. Glorioso et al. J. Virol. 50:805–812 (1984).
5. Highlander et al. J. Virol. 63:730–738 (1989).
6. Lee et al. J. Immunol. 130:1003–1006 (1983).

7. Nazerian, K. In: *Viral Oncology*, G. Klein, Ed., pp. 665–682 (1980).
8. Nazerian et al. *Avian Dis.* 33:458–465 (1989).
9. Nazerian et al. *J. Virol.* 66:1409–1413 (1992).
10. Rispens et al. *Avian Dis.* 16:108–125 (1972).
11. Ross et al. *J. Gen. Virol.* 72: 949–954 (1991).
12. Ross et al. *J. Gen. Virol.* 70:1789–1804 (1989).
13. Schat et al. *J. Nat'l. Cancer Inst.* 60:1075–1082 (1978).
14. Schat et al. *Avian Pathology* 11:593–605 (1982).
15. Silva et al. *Virology* 136:307–320 (1984).
16. Steel et al. *Principles and Procedures of Statistics*, McGraw-Hill Book Company, Inc., New York, (1960).
17. Witter *Avian Dis.* 27:113–132 (1983).
18. Witter *Avian Dis.,* 31:752–765 (1987).
19. Witter In: *Advances In Marek's Disease Research,* S. Kato et al., Eds., Japanese Association on Marek's Disease, Osaka, Japan, pp. 398–404 (1988).
20. Witter *Avian Dis.* 35:877–891 (1991).
21. Witter In: *4th International Symposium on Marek's Disease.* 19th World's Poultry Congress. Vol. 1., World's Poultry Science Assoc., Amsterdam, pp. 315–319 (1992).
22. Witter *Avian Pathology* 21:601–614 (1992).
23. Witter *Avian Pathology* 8:145–156 (1979).
24. Witter et al. *Avian Pathology* 13:75–92 (1984).
25. Witter et al. *Am J. Vet. Res.* 31:525–538 (1970).
26. Witter et al. *Avian Dis.* 24:210–232 (1980).
27. Yanagida et al. In: *4th International Symposium on Marek's Disease,* 19th World's Poultry Congress, Vol. 1., World's Poultry Science Assn., Amsterdam, pp. 44–48 (1992).
28. Yanagida et al. *J. Virol.* 66:1402–1408 (1992).
29. Yanagida et al. *J. Gen. Virol.* 74:1837–1845 (1993).
30. Yoshida et al. *Gene* 150:303–306 (1994).
31. Yoshida et al. *Virology* 200:484–493 (1994).

EXAMPLE 10

Construction of Transfer Vector pNZ29RMDgEgI

The MDV gE gene was cloned from genomic DNA of MDV strain GA by PCR. The oligonucleotide primers used for the PCR are 5'-GGGG AGATCTCATAATGTGTGTTTTCCAAATC-3' (pgE-1, SEQ ID NO:24, BglII site underlined) and 5'-GGGG GTCGACGTCCATATACTATATCCC-3' (pgE-2, SEQ ID NO:25, SalI site underlined). Primers pgE-1 and pgE-2 comprise the nucleotide sequence of the 5' terminus and 3'flanking region of the MDV gE gene, respectively (Brunnovskis et al., *Virology* 206:324–338 (1995)). A 1,558 bp DNA fragment amplified by the PCR was digested with BglII and SalI. The BglII-SalI fragment was cloned into BamHI/SalI digested pGTPs. The resulting plasmid was named pGTPsgE.

The MDV gI gene was cloned from genomic DNA of MDV strain GA by PCR. The oligonucleotide primers used for the PCR are 5'-GGGG AGATCTGCGATGTATGTACTACAATTA-3' (pgI-1, SEQ ID NO:26, BglII site underlined) and 5'-CTAACA GGTACCACCTACCTATAA-3' (pgI-2, SEQ ID NO:27, KpnI site underlined). Primers pgI-1 and pgI-2 comprise the nucleotide sequence of the 5' terminus and 3' flanking region of the MDV gE gene, respectively (Brunnovskis et al., *Virology* 206:324–338 (1995)). A 1,118 bp DNA fragment amplified by the PCR was digested with KpnI, and then partially digested with BglII. The BglII-KpnI fragment was cloned into BamHI/KpnI digested pGTPs. The resulting plasmid was named pGTPsgI. A 1,669 bp BglI fragment from pGTPs-gE was cloned into SfiI digested pNZ1829R. The resulting plasmid was named pNZ29RMDgE. A 1,232 bp BglI fragment from pGTPsgI was cloned into SfiI digested pNZ29RMDgE to obtain transfer vector pNZ29RMDgEgI.

EXAMPLE 11

Construction of Transfer Vectors pNZ29RMDgBgEgI and pNZ29RMDgBgEgIUL32

A 1,669 bp BglI fragment from pGTPsgE was cloned into SfiI digested pNZ29RMDgBSfi. The resulting plasmid was named pNZ29RMDgBgE. A 1,232 bp BglI fragment from pGTPsgI was cloned into SfiI digested pNZ29RMDgE to obtain transfer vector pNZ29RMDgBgEgI. A 2,061 bp BglI fragment from pGTPsgI was cloned into SfiI digested pNZ29RMDgBgEgI to obtain transfer vector pNZ29RMDgBgEgIUL32.

EXAMPLE 12

Generation of Recombinant FPVA recFPV/MD-gE/GI, recFPV/MD-gB/gE/gI and recFPV/MD-gB/gE/gI/UL32

Recombinants recFPV/MD-gE/gI, recFPV/MD-gB/gE/gI and recFPV/MD-gB/gE/gI/UL32 were generated by electroporation of the transfer vectors pNZ29RMDgEgI, pNZ29RMDgBgEgI and pNZ29RMDgBgEgIUL32, respectively, into host cells according to the methods described in EXAMPLE 5.

EXAMPLE 13

Protection of Antibody-Negative Chickens With Recombinant FPVs Expressing the gB Gene, or the gE and gI Genes Against a Very Virulent Strain of MDV (Md5)

Three sets of experiments were performed. Separate groups of 1-day-old chickens from 15×7 AB (−) chickens line susceptible to Marek's Disease (MD) were vaccinated with $10^5$ PFU of recFPV/MD-gB (U.S. Pat. No. 5,369,025; Example 4), $10^5$ PFU of recFPV/MD-gE/gI (Example 12), $10^5$ PFU of recFPV/MD-gBgE/gI (Example 12) or $10^5$ PFU of the USDA strain of FPV (Nazerian et al., Avian Disease 33, 458–465, (1989)). Another group of similar chickens was kept unvaccinated. All were kept in strict isolation. At 6 days of age all chickens were challenged with $5 \times 10^2$ PFU of the very virulent Md5 strain of MDV. A sixth group of chickens was neither vaccinated nor challenged. Mortality caused by MD was recorded during the trial, and the end of the 8 week trial, all chickens were examined for gross lesions and tumors typical of MD. The results of this study are presented in Table 6.

One hundred percent of unvaccinated chickens and 98% of the chickens vaccinated with the USDA of FPV died of MD before the end of the trial. On the other hand, chickens vaccinated with recFPV/MD-gE/gI were significantly well protected (PI=58%), which was similar protection observed (PI=63%) of those vaccinated with recFPV/MD-gB. Furthermore, recFPV expressing the gB, gE and gI genes conferred better protection (PI=75%).

TABLE 6

Vaccination trials to evaluate FPV recombinants
expressing the gB, gE and gI genes of MDV in AB(−) chickens
challenged with the Md5 isolate of MDV at 5 days post vaccination

|  | Trial 1 | | | | Trial 2 | | | | Trial 3 | | | | Summary | | | |
| --- | --- | --- | --- | --- | --- | --- | --- | --- | --- | --- | --- | --- | --- | --- | --- | --- |
| Vaccines | MD | test | % MD | PI | MD | test | % MD | PI | MD | test | % MD | PI | MD | test | % MD | PI |
| recFPV/MD-gB | 7 | 17 | 41 | 59 | 3 | 17 | 18 | 82 | 9 | 17 | 53 | 47 | 19 | 51 | 37 | 63 |
| recFPV/MD-gE/gI | 6 | 16 | 38 | 62 | 8 | 17 | 47 | 53 | 7 | 17 | 41 | 59 | 21 | 50 | 42 | 58 |
| recFPV/MD-gB/gE/gI | 2 | 17 | 12 | 88 | 6 | 17 | 35 | 65 | 5 | 17 | 29 | 71 | 13 | 51 | 25 | 75 |
| FPV | 16 | 16 | 100 | 0 | 13 | 14 | 93 | 7 | 16 | 16 | 100 | 0 | 45 | 46 | 98 | 2 |
| None | 16 | 16 | 100 | | 15 | 15 | 100 | | 15 | 15 | 100 | | 46 | 46 | 100 | |
| None (no chal.) | 0 | 5 | 0 | | 0 | 5 | 0 | | 0 | 5 | 0 | | 0 | 15 | 0 | |

EXAMPLE 14

Protection of Antibody-Positive Chickens With Recombinant FPVs Expressing the gB, gE and gI Genes, or the gB, gE, gI and UL32 Genes Against a Very Virulent Strain of MDV (Md5)

Three sets of experiments were performed. Separate groups of 1-day-old chickens from the 15×7 Ab (+) chicken line susceptible to MD were vaccinated with $10^5$ PFU of recFPV/MD-gB (U.S. Pat. No. 5,369,025; Example 4), $10^5$ PFU of recFPV/MD-gBgE/gI (Example 12), $10^5$ PFU of recFPV/MD-gBgE/gI/UL32 (Example 12) or $2\times10^3$ PFU of the FC126 strain of HVT (cell-associated). Another group of similar chickens was kept unvaccinated. All were kept in strict isolation. At 6 days of age all chickens were challenged with $5\times10^2$ PFU of the very virulent Md5 strain of MDV. Mortality caused by MD was recorded during the trial, and at the end of the 8 week trial, all chickens were examined for gross lesions and tumors typical of MD. The results of this study are presented in Table 7.

One hundred percent of unvaccinated chickens died of MD before the end of the trial. Forty-three percent of chickens vaccinated with recFPV/MD-gB were protected from lesions, compared to 44% of those vaccinated with HVT. The level of protection by recFPV/MD-gB/gE/gI/UL32 (PI=66%) was slightly higher than that of recFPV/MD-gB/gE/gI (PI=53%).

TABLE 7

Vaccination trials to evaluate FPV recombinants
expressing the gB, gE, gI and UL32 genes of MDV in Ab(+) chickens
challenged with the Md5 isolate of MDV at 5 days post vaccination

|  | Trial 1 | | | | Trial 2 | | | | Trial 3 | | | | Summary | | | |
| --- | --- | --- | --- | --- | --- | --- | --- | --- | --- | --- | --- | --- | --- | --- | --- | --- |
| Vaccines | MD | test | % MD | PI | MD | test | % MD | PI | MD | test | % MD | PI | MD | test | % MD | PI |
| recFPV/MD-gB | 11 | 17 | 65 | 35 | 8 | 17 | 47 | 53 | 10 | 17 | 59 | 41 | 29 | 51 | 57 | 43 |
| recFPV/MD-gB/gE/gI | 6 | 16 | 38 | 62 | 9 | 16 | 56 | 44 | 8 | 17 | 47 | 53 | 23 | 49 | 47 | 53 |
| recFPV/MD-gB/gE/gI/UL32 | 5 | 17 | 29 | 71 | 5 | 17 | 29 | 71 | 7 | 16 | 44 | 56 | 17 | 50 | 34 | 66 |
| HVT | 9 | 17 | 53 | 47 | 9 | 17 | 53 | 47 | 10 | 16 | 63 | 37 | 28 | 50 | 56 | 44 |
| None | 16 | 16 | 100 | | 17 | 17 | 100 | | 16 | 16 | 100 | | 49 | 49 | 100 | |

What is claimed is:

1. A vaccine composition comprising
   a recombinant virus comprising an isolated, purified DNA molecule comprising
   (a) the nucleotide sequence shown in SEQ ID NO:1, or a nucleotide sequence biologically functionally equivalent to SEQ ID NO: 1, and
   (b) gB antigen of Marek's disease virus or a polypeptide biologically functionally equivalent thereto; or
   a virus comprising
   (a) an isolated, purified DNA molecule comprising a nucleotide sequence encoding a polypeptide comprising the amino acid sequence as shown in SEQ ID NO:2, or comprising an amino acid sequence biologically functionally equivalent to SEQ ID NO: 2, and
   (b) gB antigen of Marek's disease virus or a polypeptide biologically functionally equivalent thereto;
   and a pharmaceutically acceptable carrier.

2. A vaccine composition comprising
   a recombinant virus comprising
   (a) an isolated, purified DNA molecule comprising the nucleotide sequence shown in SEQ ID NO:1, or comprising a nucleotide sequence biologically functionally equivalent to SEQ ID NO: 1,
   (b) a gB antigen of Marek's disease virus or a polypeptide biologically functionally equivalent thereto, and
   (c) a gE antigen of Marek's disease virus or a polypeptide biologically functionally equivalent thereto; or
   a recombinant virus comprising
   (a) an isolated, purified DNA molecule comprising a nucleotide sequence encoding a polypeptide comprising the amino acid sequence as shown in SEQ ID NO:2, or comprising an amino acid sequence biologically functionally equivalent to SEQ ID NO: 2,
   (b) gB antigen of Marek's disease virus or a polypeptide biologically functionally equivalent thereto, and
   (c) a gE antigen of Marek's disease virus or a polypeptide biologically functionally equivalent thereto;
   and a pharmaceutically acceptable carrier.

3. A vaccine composition comprising
   a recombinant virus comprising
   (a) an isolated, purified DNA molecule comprising the nucleotide sequence shown in SEQ ID NO:1, or a nucleotide sequence biologically functionally equivalent to SEQ ID NO: 1,
   (b) a gB antigen of Marek's disease virus or a polypeptide biologically functionally equivalent thereto,
   (c) a gE antigen of Marek's disease virus or a polypeptide biologically functionally equivalent thereto, and
   (d) a gI antigen of Marek's disease virus or a polypeptide biologically functionally equivalent thereto; or
   a recombinant virus comprising
   (a) an isolated, purified DNA molecule comprising a nucleotide sequence encoding a polypeptide comprising the amino acid sequence as shown in SEQ ID NO:2, or comprising an amino acid sequence biologically functionally equivalent to SEQ ID NO:2,
   (b) a gB antigen of Marek's disease virus or a polypeptide biologically functionally equivalent thereto,
   (c) a gE antigen of Marek's disease virus or a polypeptide biologically functionally equivalent thereto, and
   (d) a gI antigen of Marek's disease virus or a polypeptide biologically functionally equivalent thereto;

and a pharmaceutically acceptable carrier.

4. The vaccine composition of claim 1, wherein said isolated, purified nucleotide sequences comprise the nucleotide sequence shown in SEQ ID NO:1, or a nucleotide sequence encoding a polypeptide comprising the amino acid sequence as shown in SEQ ID NO:2.

5. The vaccine composition of claim 2, wherein said isolated, purified nucleotide sequences comprise the nucleotide sequence shown in SEQ ID NO:1, or a nucleotide sequence encoding a polypeptide comprising the amino acid sequence as shown in SEQ ID NO:2.

6. The vaccine composition of claim 3, wherein said isolated, purified nucleotide sequences comprise the nucleotide sequence shown in SEQ ID NO:1, or a nucleotide sequence encoding a polypeptide comprising the amino acid sequence as shown in SEQ ID NO:2.

7. A vaccine composition, comprising a recombinant virus expressing an isolated, purified nucleotide sequence encoding a Marek's disease virus polypeptide or a polypeptide biologically functionally equivalent to SEQ ID NO:2, in combination with a herpes virus, wherein said vaccine composition exhibits an immunoprotective effect greater than the sum of the individual immunoprotective effects of vaccine compositions individually comprising each of said viruses;

and a pharmaceutically acceptable carrier.

8. The vaccine composition of claim 7, wherein said recombinant virus is fowlpox virus expressing Marek's disease virus gB protein, and said herpesvirus is turkey herpesvirus.

9. The vaccine composition of claim 7, wherein said recombinant virus is fowlpox virus expressing Marek's disease virus gB protein and Marek's disease virus gE protein, and said herpesvirus is turkey herpesvirus.

10. The vaccine composition of claim 7, wherein said recombinant virus is fowlpox virus expressing Marek's disease virus gB protein, Marek's disease virus gE protein and Marek's disease virus gI protein, and said herpesvirus is turkey herpesvirus.

11. The vaccine composition of claim 8, wherein said gB protein is of serotype 1.

12. The vaccine composition of claim 9, wherein said gB protein and gE protein are both of serotype 1.

13. The vaccine composition of claim 10, wherein said gB, gE and gI protein are all of serotype 1.

14. A vaccine composition comprising a DNA molecule comprising the sequence shown in SEQ ID NO:1; or a recombinant vector comprising a DNA molecule comprising the sequence shown in SEQ ID NO:1; or a recombinant virus or viruses comprising a DNA molecule comprising the sequence shown in SEQ ID NO:1, or a nucleotide sequence biologically functionally equivalent to SEQ ID NO:1, as well as a DNA sequence encoding at least one antigen of an avian pathogen or an antigen or pathogen biologically functionally equivalent thereto;

and a polypeptide having the amino acid sequence shown in SEQ ID NO:2;

and a pharmaceutically acceptable carrier.

15. A method of immunizing poultry, comprising administring to said poultry the vaccine composition of claim 18.

* * * * *

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 1925 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
ATGGCCAACC GCCCTACAGA GTTGGCAGCT TTTATCCGAT CTTCTGGAGA AGCAGATGGA      60
TGGATAGAGG AGTCCTTCAA AGAACCCTAT GTGGCATTTA ATCCGGACGT CTTGATGTAT     120
AATGACACGC TTTTTAACGA GTTATTACTC TCCGCCCACG CGCTCAAGAT CAACAGTATA     180
CAGGATGTTC AGAGTGATGA TACCGTGGAG GATGCGGGAG ATATTGGGAA TGAAGTTATA     240
CATTCGGAAT TAGTAACTTT TATAGAGACT GCTGCAGATG TTTATGCCTT AGATCGTCAA     300
TGCCTTGTTT GTCGTGTGCT AGATATGTAC AGGCGCAATT TCGGTTTATC AGCTCTATGG     360
ATGGCAGATT ATGCTTTTTT ATGTTCCAAA TGTCTTGGTT CTCCACCATG TGCAACTGCA     420
ACCTTTATAG CCGCGTTTGA ATTCGTATAT ATAATGGATA AACACTTTCT ATCCGATCAT     480
GGTTGTACAC TCGTACGCTC CTTTGGAAAA AAACTTTTAA CTCTCGAAGA TATTCAGAGA     540
CATTTTTTTC TGCATGGCTG TTTTCGAACG GACGGGGGCG TTCCTGGACG ACGCCATGAT     600
GAAGTTATTA CGTCTCGTTC TAAGCAAGGA CGATTAGTAG GGCGACGTGG GAAATTTTCT     660
ACTGCGGGTG ATGCCAAAGT CTTGTACAGT AATTACTCAT ATTTAGCTCA GAGTGCTACA     720
CGAGCCCTGT TAATGACCTT ATCTGATTTA GGTTCTGCAC CGCTAGAAGT TATCGAAGGG     780
CGACAAAAGT CTATTTCGGG GGATGTTCGA AATGAGTTGA GGGATGGCAT AGAGAGTAGG     840
AAAAGGGTCG CGCATGTCAT TCATTCCGTT GGACCAGTCC ACTCATGCCC AACTACTCTT     900
TCCGTTGCTT TGGCGGGCTG GAAAGATTGT GCTAAAAACG TAGAATGTAA CTTTTTTCAA     960
CTGGAAAGTT GTACTTTGCG CGCATCGTCC GAGGATAATG ATTATGAACA CGAGTGGGAA    1020
CTCCGAGCAA GTGAAGAAAA GTTAAATGTG GTGGAAAATG TTCAGGACAT GCAACAGATA    1080
GATGCGTCTC AATGCGAACA TCATGAACAT GCAAGAAATG AGGATTGTAC AATGGGTTAT    1140
GGCAACCTCG TTTTATTGTT ATTAGCGGGA ACGGGGTCTG CACCTGAGGC AGCGAGCGAA    1200
CTCGCATTCA TGGCCGCAAA AGTTAGAAGG GAAACGGTGG ATATATTTTG GAAAAATCAT    1260
AGAAGGGAAT TTGCTAATGA CGTTACTGCA GCATACAGTG CATGTTACGG TGAGGATTCG    1320
GAACCCGATT TAGAGTTAGG CCCATTGATG ATAACACAGT TAAAGCACGC GATAACAAAA    1380
GGAGGAACAT CTGCGGAGTG TTTATTATGT AACCTGCTGC TGATACGTAC ATATTGGCTG    1440
GCAATGCGTA AATTTAAACG CGATATCATC ACATATTCCG CCAACAATAT AGGTTTATTT    1500
CATAGCATAG AACCTGTTCT AGATGCTTGG CGATCACAGG GACATCGTAC AGATTTGGGG    1560
GACGAAGGAT GTTTTGTAAC ATTAATGAAA AGCGCGGGAA CGGAGGCCAT TTATAAACAC    1620
CTATTCTGCG ATCCAATGTG TGCGGCACGA ATAGCCCAGA CCAATCCACG ATCGTTATTT    1680
GATCACCCAG ATGCCACCAA TCATGACGAA CTAGCATTAT ATAAAGCCCG TCTCGCCAGT    1740
CAGAACCATT TTGAAGGTCG CGTATGTGCT GGACTTTGGG CTTTGGCGTA TACGTTTAAA    1800
ACTTATCAGG TCTTTCCTCC CCGTCAACCG CACTGTCTGC TTTCGTTAAA GACGCTGGGG    1860
CATTGTTGCA AAGACATTCC ATCTCCTTGA TATCTCTCGA GCATACATTA GGAGTCTACG    1920
TGTAA                                                                1925
```

(2) INFORMATION FOR SEQ ID NO:2:

(i) SEQUENCE CHARACTERISTICS:
        (A) LENGTH: 641 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
Met Ala Asn Arg Pro Thr Glu Leu Ala Ala Phe Ile Arg Ser Ser Gly
1               5                   10                  15

Glu Ala Asp Gly Trp Ile Glu Glu Ser Phe Lys Glu Pro Tyr Val Ala
            20                  25                  30

Phe Asn Pro Asp Val Leu Met Tyr Asn Asp Thr Leu Phe Asn Glu Leu
        35                  40                  45

Leu Leu Ser Ala His Ala Leu Lys Ile Asn Ser Ile Gln Asp Val Gln
    50                  55                  60

Ser Asp Thr Val Glu Asp Ala Gly Asp Ile Gly Asn Glu Val Ile
65                  70                  75                  80

His Ser Glu Leu Val Thr Phe Ile Glu Thr Ala Ala Asp Val Tyr Ala
                85                  90                  95

Leu Asp Arg Gln Cys Leu Val Cys Arg Val Leu Asp Met Tyr Arg Arg
            100                 105                 110

Asn Phe Gly Leu Ser Ala Leu Trp Met Ala Asp Tyr Ala Phe Leu Cys
        115                 120                 125

Ser Lys Cys Leu Gly Ser Pro Pro Cys Ala Thr Ala Thr Phe Ile Ala
    130                 135                 140

Ala Phe Glu Phe Val Tyr Ile Met Asp Lys His Phe Leu Ser Asp His
145                 150                 155                 160

Gly Cys Thr Leu Val Arg Ser Phe Gly Lys Lys Leu Leu Thr Leu Glu
                165                 170                 175

Asp Ile Gln Arg His Phe Phe Leu His Gly Cys Phe Arg Thr Asp Gly
            180                 185                 190

Gly Val Pro Gly Arg Arg His Asp Glu Val Ile Thr Ser Arg Ser Lys
        195                 200                 205

Gln Gly Arg Leu Val Gly Arg Arg Gly Lys Phe Ser Thr Ala Gly Asp
    210                 215                 220

Ala Lys Val Leu Tyr Ser Asn Tyr Ser Tyr Leu Ala Gln Ser Ala Thr
225                 230                 235                 240

Arg Ala Leu Leu Met Thr Leu Ser Asp Leu Gly Ser Ala Pro Leu Glu
                245                 250                 255

Val Ile Glu Gly Arg Gln Lys Ser Ile Ser Gly Asp Val Arg Asn Glu
            260                 265                 270

Leu Arg Asp Gly Ile Glu Ser Arg Lys Arg Val Ala His Val Ile His
        275                 280                 285

Ser Val Gly Pro Val His Ser Cys Pro Thr Thr Leu Ser Val Ala Leu
    290                 295                 300

Ala Gly Trp Lys Asp Cys Ala Lys Asn Val Glu Cys Asn Phe Phe Gln
305                 310                 315                 320

Leu Glu Ser Cys Thr Leu Arg Ala Ser Ser Glu Asp Asn Asp Tyr Glu
                325                 330                 335

His Glu Trp Glu Leu Arg Ala Ser Glu Glu Lys Leu Asn Val Val Glu
            340                 345                 350

Asn Val Gln Asp Met Gln Gln Ile Asp Ala Ser Gln Cys Glu His His
        355                 360                 365

Glu His Ala Arg Asn Glu Asp Cys Thr Met Gly Tyr Gly Asn Leu Val
    370                 375                 380
```

```
Leu Leu Leu Leu Ala Gly Thr Gly Ser Ala Pro Glu Ala Ala Ser Glu
385                 390                 395                 400

Leu Ala Phe Met Ala Ala Lys Val Arg Arg Glu Thr Val Asp Ile Phe
            405                 410                 415

Trp Lys Asn His Arg Arg Glu Phe Ala Asn Asp Val Thr Ala Ala Tyr
            420                 425                 430

Ser Ala Cys Tyr Gly Glu Asp Ser Glu Pro Asp Leu Glu Leu Gly Pro
            435                 440                 445

Leu Met Ile Thr Gln Leu Lys His Ala Ile Thr Lys Gly Gly Thr Ser
450                 455                 460

Ala Glu Cys Leu Leu Cys Asn Leu Leu Leu Ile Arg Thr Tyr Trp Leu
465                 470                 475                 480

Ala Met Arg Lys Phe Lys Arg Asp Ile Ile Thr Tyr Ser Ala Asn Asn
            485                 490                 495

Ile Gly Leu Phe His Ser Ile Glu Pro Val Leu Asp Ala Trp Arg Ser
            500                 505                 510

Gln Gly His Arg Thr Asp Leu Gly Asp Glu Gly Cys Phe Val Thr Leu
            515                 520                 525

Met Lys Ser Ala Gly Thr Glu Ala Ile Tyr Lys His Leu Phe Cys Asp
530                 535                 540

Pro Met Cys Ala Ala Arg Ile Ala Gln Thr Asn Pro Arg Ser Leu Phe
545                 550                 555                 560

Asp His Pro Asp Ala Thr Asn His Asp Glu Leu Ala Leu Tyr Lys Ala
            565                 570                 575

Arg Leu Ala Ser Gln Asn His Phe Glu Gly Arg Val Cys Ala Gly Leu
            580                 585                 590

Trp Ala Leu Ala Tyr Thr Phe Lys Thr Tyr Gln Val Phe Pro Pro Arg
            595                 600                 605

Xaa Thr Ala Leu Ser Ala Phe Val Lys Asp Ala Gly Ala Leu Leu Gln
            610                 615                 620

Arg His Ser Ile Ser Leu Ile Ser Leu Glu His Thr Leu Gly Val Tyr
625                 630                 635                 640

Val
```

(2) INFORMATION FOR SEQ ID NO:3:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
TTTTTTTTTT TTTTTTTTTT GGCATATAAA TAATAAATAC AATAATTAAT TACGCGTAAA     60

AATTGAAAAA CTATTCTAAT TTATTGCACT C                                    91
```

(2) INFORMATION FOR SEQ ID NO:4:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GGYCAATCT                                                                                      9

(2) INFORMATION FOR SEQ ID NO:5:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

AGCTGCCCCC CCGGCAAGTT GCA                                                                     23

(2) INFORMATION FOR SEQ ID NO:6:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

TCGACATTTT TATGTAC                                                                            17

(2) INFORMATION FOR SEQ ID NO:7:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

AATTCGGCCG GGGGGGCCAG CT                                                                      22

(2) INFORMATION FOR SEQ ID NO:8:

(i) SEQUENCE CHARACTERISTICS:
             (A) LENGTH: 14 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GGCCCCCCCG GCCG                                                              14

(2) INFORMATION FOR SEQ ID NO:9:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

CCCCGGATCC GGCCATGGCC AACCGC                                                 26

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:10:

AAGAATGCAT AATCTGCCAT CCAT                                                   24

(2) INFORMATION FOR SEQ ID NO:11:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

GATTATGCAT TCTTATGTTC CAAATC                                                 26

(2) INFORMATION FOR SEQ ID NO:12:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:12:

ACAGCCATGG AGAAAGAAAT GTCTCTGAAT ATC                                    33

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

TTCTCCATGG CTGTTTTCGA ACG                                              23

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:14:

CCCCGTCGAC TTACACGTAG ACTCCTAATG                                        30

(2) INFORMATION FOR SEQ ID NO:15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

TATGCTTTTT TATGT                                                       15

(2) INFORMATION FOR SEQ ID NO:16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

```
TATGCATTCT TATGT                                                    15
```

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:17:

```
Tyr Ala Phe Leu Cys
1               5
```

(2) INFORMATION FOR SEQ ID NO:18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

```
TATGCTTTTT TATGT                                                    15
```

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

```
CATTTTTTTC TGCATGGC                                                 18
```

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

```
CATTTCTTTC TCCATGGC                                                 18
```

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:21:

```
His Phe Phe Leu His Gly
1               5
```

(2) INFORMATION FOR SEQ ID NO:22:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

```
GGCCCCCCCG GCCG                                                        14
```

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

```
AATTCGGCCGG GGGGGCCAGC T                                               22
```

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "pgE-1 PCR primer for MDV gE gene"

(iii) HYPOTHETICAL: NO (iv) ANTI-SENSE: NO (xi) SEQUENCE DESCRIPTION: SEQ ID NO:24:

```
GGGGAGATCT CATAATGTGT GTTTTCCAAA TC                                    32
```

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "pgE-2 PCR primer for MDV gE gene"

(iii) HYPOTHETICAL: NO (iv) ANTI-SENSE: YES (xi) SEQUENCE DESCRIPTION: SEQ ID NO:25:

GGGGGTCGAC GTCCATATAC TATATCCC                                28

(2) INFORMATION FOR SEQ ID NO:26:

(i) SEQUENCE CHARACTERISTICS:
        (A) LENGTH: 31 base pairs
        (B) TYPE: nucleic acid
        (C) STRANDEDNESS: Not Relevant
        (D) TOPOLOGY: Not Relevant (ii) MOLECULE TYPE: other nucleic acid
        (A) DESCRIPTION: /desc = "pgI-1 PCR primer for MDV gI gene"

(iii) HYPOTHETICAL: NO (iv) ANTI-SENSE: NO (xi) SEQUENCE DESCRIPTION: SEQ ID NO:26:

GGGGAGATCT GCGATGTATG TACTACAATT A                           31

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "pgI-2 PCR primer for MDV gI gene"

(iii) HYPOTHETICAL: NO (iv) ANTI-SENSE: YES (xi) SEQUENCE DESCRIPTION: SEQ ID NO:27:

CTAACAGGTA CCACCTACCT ATAA                                      24

(2) INFORMATION FOR SEQ ID NO:28:

(i) SEQUENCE CHARACTERISTICS:
        (A) LENGTH: 355 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Marek's disease virus type I
        (B) STRAIN: GA (ix) FEATURE:

(A) NAME/KEY: Protein
(B) LOCATION: 1..355
(D) OTHER INFORMATION: /label= protein /note= "gI protein"

(xi) SEQUENCE DESCRIPTION: SEQ ID NO:28:

Met Tyr Val Leu Gln Leu Leu Phe Trp Ile Arg Leu Phe Arg Gly Ile
1               5                   10                  15

Trp Ser Ile Val Tyr Thr Gly Thr Ser Val Thr Leu Ser Thr Asp Gln
            20                  25                  30

Ser Ala Leu Val Ala Phe Cys Gly Leu Asp Lys Met Val Asn Val Arg
        35                  40                  45

Gly Gln Leu Leu Phe Leu Gly Asp Gln Thr Arg Thr Ser Ser Tyr Thr
    50                  55                  60

Gly Thr Thr Glu Ile Leu Lys Trp Asp Glu Glu Tyr Lys Cys Tyr Ser
65                  70                  75                  80

Val Leu His Ala Thr Ser Tyr Met Asp Cys Pro Ala Ile Asp Ala Thr
                85                  90                  95

Val Phe Arg Gly Cys Arg Asp Ala Val Val Tyr Ala Gln Pro His Asp
            100                 105                 110

Arg Val Gln Pro Phe Pro Glu Lys Gly Thr Leu Leu Arg Ile Val Glu
        115                 120                 125

Pro Arg Val Ser Asp Thr Gly Ser Tyr Tyr Ile Arg Val Ala Leu Ala
    130                 135                 140

Gly Arg Asn Met Ser Asp Ile Phe Arg Met Ala Val Ile Ile Arg Ser
145                 150                 155                 160

Ser Lys Ser Trp Ala Cys Asn His Ser Ala Ser Phe Gln Ala His
                165                 170                 175

Lys Cys Ile Arg Tyr Val Asp Arg Met Ala Phe Glu Asn Tyr Leu Ile
            180                 185                 190

Gly His Val Gly Asn Leu Leu Asp Ser Asp Ser Glu Leu His Ala Ile
        195                 200                 205

Tyr Asn Ile Thr Pro Gln Ser Ile Ser Thr Asp Ile Asn Ile Ile Thr
    210                 215                 220

Thr Pro Phe Tyr Asp Asn Ser Gly Thr Ile Tyr Ser Pro Thr Val Phe
225                 230                 235                 240

Asn Leu Phe Asn Asn Ser His Val Asp Ala Met Asn Ser Thr Gly
                245                 250                 255

Met Trp Asn Thr Val Leu Lys Tyr Thr Leu Pro Arg Leu Ile Tyr Phe
            260                 265                 270

Ser Thr Met Ile Val Leu Cys Ile Ile Ala Leu Ala Ile Tyr Leu Val
        275                 280                 285

Cys Glu Arg Cys Arg Ser Pro His Arg Arg Ile Tyr Ile Gly Glu Pro
    290                 295                 300

Arg Ser Asp Glu Ala Pro Leu Ile Thr Ser Ala Val Asn Glu Ser Phe
305                 310                 315                 320

Gln Tyr Asp Tyr Asn Val Lys Glu Thr Pro Ser Asp Val Ile Glu Lys
                325                 330                 335

Glu Leu Met Glu Lys Leu Lys Lys Val Glu Leu Leu Glu Arg Glu
            340                 345                 350

Glu Cys Val
        355

(2) INFORMATION FOR SEQ ID NO:29:

(i) SEQUENCE CHARACTERISTICS:

-continued (A) LENGTH: 497 amino acids
(B) TYPE: amino acid
(C) STRANDEDNESS: Not Relevant
(D) TOPOLOGY: linear (ii) MOLECULE TYPE: protein (iii) HYPOTHETICAL: NO (v) FRAGMENT TYPE: internal (vi) ORIGINAL SOURCE:
(A) ORGANISM: Marek's disease virus type I
(B) STRAIN: GA (ix) FEATURE:
(A) NAME/KEY: Protein
(B) LOCATION: 1..497
(D) OTHER INFORMATION: /label= protein /note= "gE protein"

(xi) SEQUENCE DESCRIPTION: SEQ ID NO:29:

```
Met Cys Val Phe Gln Ile Leu Ile Ile Val Thr Thr Ile Lys Val Ala
1               5                   10                  15

Gly Thr Ala Asn Ile Asn His Ile Asp Val Pro Ala Gly His Ser Ala
            20                  25                  30

Thr Thr Thr Ile Pro Arg Tyr Pro Pro Val Val Asp Gly Thr Leu Tyr
        35                  40                  45

Thr Glu Thr Trp Thr Trp Ile Pro Asn His Cys Asn Glu Thr Ala Thr
    50                  55                  60

Gly Tyr Val Cys Leu Glu Ser Ala His Cys Phe Thr Asp Leu Ile Leu
65                  70                  75                  80

Gly Val Ser Cys Met Arg Tyr Ala Asp Glu Ile Val Leu Arg Thr Asp
                85                  90                  95

Lys Phe Ile Val Asp Ala Gly Ser Ile Lys Gln Ile Glu Ser Leu Ser
            100                 105                 110

Leu Asn Gly Val Pro Asn Ile Phe Leu Ser Thr Lys Ala Ser Asn Lys
        115                 120                 125

Leu Glu Ile Leu Asn Ala Ser Leu Gln Asn Ala Gly Ile Tyr Ile Arg
    130                 135                 140

Tyr Ser Arg Asn Gly Asp Glu Asp Cys Lys Leu Asp Val Val Val Val
145                 150                 155                 160

Gly Val Leu Gly Gln Ala Arg Asp Arg Leu Arg Gln Met Ser Ser Pro
                165                 170                 175

Met Ile Ser Ser His Ala Asp Ile Lys Leu Ser Leu Lys Asn Phe Lys
            180                 185                 190

Ala Leu Val Tyr His Val Gly Asp Thr Ile Asn Val Ser Thr Ala Val
        195                 200                 205

Ile Leu Gly Pro Ser Pro Glu Ile Phe Thr Leu Glu Phe Arg Val Leu
    210                 215                 220

Phe Leu Arg Tyr Asn Pro Thr Cys Lys Phe Val Thr Ile Tyr Glu Pro
225                 230                 235                 240

Gly Ile Phe His Pro Lys Glu Pro Glu Gly Ile Thr Thr Ala Glu Gln
                245                 250                 255

Ser Val Cys His Phe Ala Ser Asn Ile Asp Ile Leu Gln Ile Ala Ala
            260                 265                 270

Ala Arg Ser Glu Asn Cys Ser Thr Gly Tyr Arg Arg Cys Ile Tyr Asp
        275                 280                 285

Thr Ala Ile Asp Glu Ser Val Gln Ala Arg Leu Thr Phe Ile Glu Pro
    290                 295                 300
```

-continued

```
Gly Ile Pro Ser Phe Lys Met Lys Asp Val Gln Val Asp Asp Ala Gly
305                 310                 315                 320

Leu Tyr Val Val Ala Leu Tyr Asn Gly Arg Pro Ser Ala Trp Thr
            325                 330                 335

Tyr Ile Tyr Leu Ser Thr Val Glu Thr Tyr Leu Asn Val Tyr Glu Asn
            340                 345                 350

Tyr His Lys Pro Gly Phe Gly Tyr Lys Ser Phe Leu Gln Asn Ser Ser
        355                 360                 365

Ile Ile Asp Glu Asp Glu Ala Ser Asp Trp Ser Ser Ser Ser Ile Lys
    370                 375                 380

Arg Arg Asn Asn Gly Thr Ile Leu Tyr Asp Ile Leu Leu Thr Ser Leu
385                 390                 395                 400

Ser Ile Gly Ala Ile Ile Val Ile Val Gly Gly Val Cys Ile Ala
            405                 410                 415

Ile Leu Ile Arg Arg Arg Arg Arg Arg Thr Arg Gly Leu Phe Asp
            420                 425                 430

Glu Tyr Pro Lys Tyr Met Thr Leu Pro Gly Asn Asp Leu Gly Gly Met
        435                 440                 445

Asn Val Pro Tyr Asp Asn Ala Cys Ser Gly Asn Gln Val Glu Tyr Tyr
    450                 455                 460

Gln Glu Lys Ser Asp Lys Met Lys Arg Met Gly Ser Gly Tyr Thr Ala
465                 470                 475                 480

Trp Leu Lys Asn Asp Met Pro Lys Ile Arg Lys Arg Leu Asp Leu Tyr
            485                 490                 495

His
```